(12) United States Patent
Akhtar et al.

(10) Patent No.: US 12,336,918 B2
(45) Date of Patent: Jun. 24, 2025

(54) SYSTEM AND METHOD FOR AN ARTIFICIAL TENDON-DRIVEN PROSTHESIS

(71) Applicant: PSYONIC, Inc., Urbana, IL (US)

(72) Inventors: Aadeel Akhtar, Urbana, IL (US); James Austin, Champaign, IL (US); Dhipak Bala, Urbana, IL (US); Valentino Wilson, Champaign, IL (US)

(73) Assignee: PSYONIC, Inc., Champaign, IL (US)

( * ) Notice: Subject to any disclaimer, the term of this patent is extended or adjusted under 35 U.S.C. 154(b) by 0 days.

(21) Appl. No.: 17/670,199

(22) Filed: Feb. 11, 2022

(65) Prior Publication Data
US 2022/0249257 A1 Aug. 11, 2022

Related U.S. Application Data

(60) Provisional application No. 63/176,764, filed on Apr. 19, 2021, provisional application No. 63/148,378, filed on Feb. 11, 2021.

(51) Int. Cl.
*A61F 2/58* (2006.01)
*A61F 2/50* (2006.01)
(Continued)

(52) U.S. Cl.
CPC ............ *A61F 2/586* (2013.01); *A61F 2/76* (2013.01); *A61F 2/78* (2013.01); *A61F 2002/5038* (2013.01); *A61F 2002/6872* (2013.01)

(58) Field of Classification Search
CPC .... A61F 2/08; A61F 2/54; A61F 2/586; A61F 2/76; A61F 2/78; A61F 2002/5038; A61F 2002/587; A61F 2002/6872
See application file for complete search history.

(56) References Cited

U.S. PATENT DOCUMENTS

| | | | |
|---|---|---|---|
| 4,143,426 A | 3/1979 | Hall et al. | |
| 11,185,427 B2 | 11/2021 | Akhtar et al. | |

(Continued)

FOREIGN PATENT DOCUMENTS

| | | | | |
|---|---|---|---|---|
| DE | 327490 C | * | 5/1916 | ............. A61F 2/586 |
| GB | 2488760 A | * | 9/2012 | ............. A61F 2/583 |
| WO | 2015193856 A1 | | 12/2015 | |

OTHER PUBLICATIONS

Translation of DE327490-C (Year: 1916).*
U.S. Appl. No. 17/512239, filed Oct. 27, 2021, Aadeel Akhtar.

*Primary Examiner* — Christie Bahena
(74) *Attorney, Agent, or Firm* — Alpine Patents LLC; Brian Van Osdol

(57) ABSTRACT

A system and method for an artificial tendon or muscle driven prosthesis that may include an articulating prosthesis with a set of actuation points; an artificial tendon system, the artificial tendon system being integrated with the articulating prosthesis and comprising an external tendon actuation interface coupled relative to at least one actuation point of the set of actuation points, and the artificial tendon system further comprising integration with a musculoskeletal-integrated internal artificial tendon; and an osseointegration abutment through which the artificial tendon system couples the external tendon actuation interface to the musculoskeletal-integrated internal artificial tendon integration and can implement an infection mitigation system.

17 Claims, 19 Drawing Sheets

(51) Int. Cl.
*A61F 2/76* (2006.01)
*A61F 2/78* (2006.01)
*A61F 2/68* (2006.01)

(56) References Cited

U.S. PATENT DOCUMENTS

| | | |
|---|---|---|
| 2005/0021154 A1 | 1/2005 | Brimalm |
| 2010/0036507 A1 | 2/2010 | Gow |
| 2010/0082103 A1 | 4/2010 | Blunn et al. |
| 2011/0160873 A1 | 6/2011 | Jaworski |
| 2013/0053984 A1 | 2/2013 | Hunter et al. |
| 2014/0277588 A1 | 9/2014 | Patt et al. |
| 2014/0277589 A1 | 9/2014 | Veatch |
| 2015/0230941 A1 | 8/2015 | Jury |
| 2016/0250015 A1 | 9/2016 | Kim et al. |
| 2017/0007424 A1 | 1/2017 | Gill |
| 2017/0020691 A1 | 1/2017 | Thompson et al. |
| 2020/0306059 A1 | 10/2020 | Cornman et al. |
| 2021/0085491 A1 | 3/2021 | Akhtar et al. |
| 2021/0293643 A1 | 9/2021 | Correll et al. |
| 2022/0183862 A1 | 6/2022 | Akhtar et al. |

\* cited by examiner

SYSTEM AND METHOD FOR AN ARTIFICIAL TENDON-DRIVEN PROSTHESIS

CROSS-REFERENCE TO RELATED APPLICATIONS

This Application claims the benefit of U.S. Provisional Application No. 63/148,378, filed on 11 Feb. 2021, and U.S. Provisional Application No. 63/176,764, filed on 19 Apr. 2021, both of which are incorporated in their entireties by this reference.

TECHNICAL FIELD

This invention relates generally to the field of prostheses, and more specifically to a new and useful systems and methods for an artificial tendon or muscle driven prosthesis.

BACKGROUND

In recent years, significant progress has been made in the development of multiarticulated prosthetic fingers and hands. The state-of-the-art for prosthetic limbs are electric powered prostheses, controlled using muscle sensors placed over the residual limb of the user. These devices can often be heavy and uncomfortable to the user. Furthermore, being electric-based devices, they often depend on batteries. Furthermore, such prostheses lack proprioceptive feedback to the user. As a result, users often have to rely primarily on vision to know the position and orientation of their prosthesis. Surveys have reported that this over-dependence on vision is one of the largest contributors to prosthesis abandonment.

Thus, there is a need in the prosthesis field to create a new and useful systems and methods for an artificial tendon-driven prosthesis. This invention provides such a new and useful systems and methods.

DESCRIPTION OF THE EMBODIMENTS

Figure 1A:
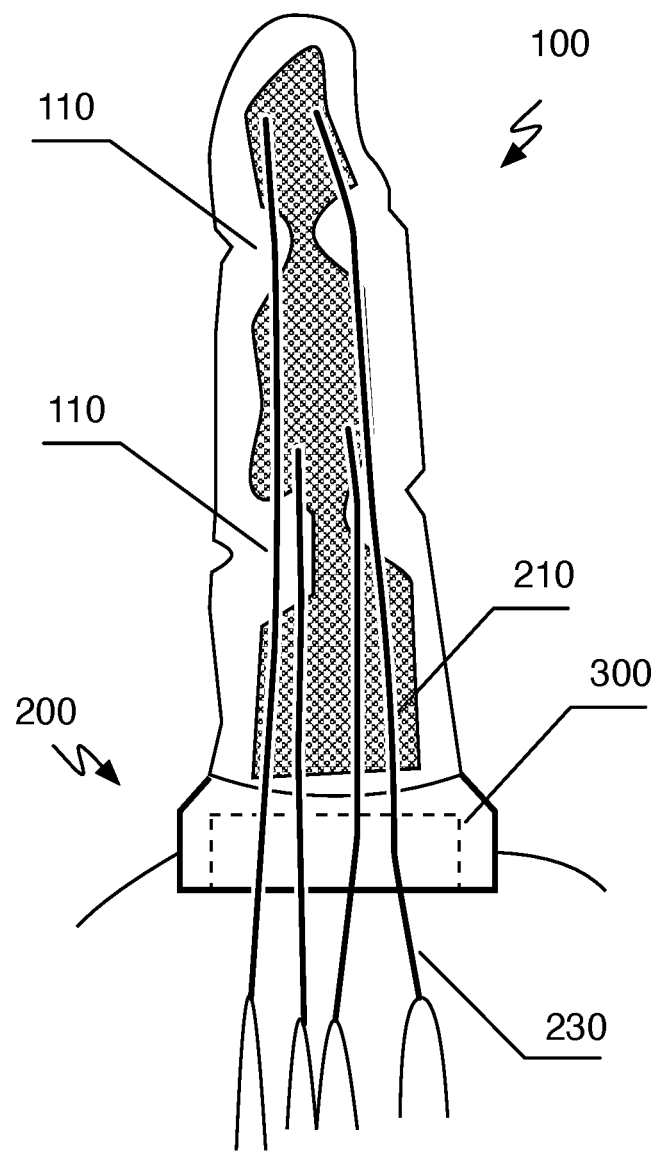
FIG. 1A is a schematic representation of a system variation of an articulating prosthesis and artificial tendon system.

The following description of the embodiments of the invention is not intended to limit the invention to these embodiments but rather to enable a person skilled in the art to make and use this invention.

1. Overview

Systems and methods for artificial tendon- and/or muscle-driven prostheses function to enable a biointegrated prosthesis that is driven at least partially through biomechanical movement of a user. More specifically, the systems and methods can enable an artificial tendon system to attach an external prosthesis to existing tendons. The prosthesis of the systems and methods can include an actuating prosthesis system that actuates at least in part in response to mechanical coupling to residual tendons, muscles, and/or bone of a user. The systems and methods may enable an artificial tendon/muscle-driven prosthesis that may be substantially anatomically accurate (e.g., biomechanically and/or anthropometrically) and osseointegrated.

The systems and methods may provide a functional, actuating prosthesis that integrates with an individual's residual tendon(s), muscles, and/or bone. The prosthesis of the systems and methods may enable users to control their prosthesis directly from their muscles, with proprioception, and in a biomechanically natural way. Variations of the systems and methods may enable an actuating prosthesis that is biologically actuated and battery-free. Other variations may make use of electromechanical and/or other electrical based systems to facilitate locomotion of the prosthesis or to otherwise enable other features, which may make use of a battery or other electrical power source.

The systems and methods, in some embodiments can include the artificial tendon (AT) system and the prosthesis described herein.

The systems and methods, in some embodiments, may alternatively include the prosthesis described herein, which can be compatible with the AT system described herein or other suitable AT systems (artificial tendon systems).

The systems and methods, in some embodiments, may alternatively include the AT system described herein, which can be compatible with a prosthesis such as described herein or other suitable prostheses.

Herein, the systems and methods are primarily described as they would be implemented with a prosthesis in combination with an AT system, but any variation described for each component may alternatively be implemented as part of a stand-alone subsystem used with an external system.

The systems and methods may make use of artificial tendon fibers, potentially, less than 50 μm in diameter and of a material that will provide the necessary biocompatibility and tensile properties. The artificial tendon fibers are fused or attached to the biological tendon and/or muscle, and then coupled through an osseointegration abutment that attaches the biological bone to an external tendon-actuated prosthesis.

Other variations of the systems and methods may make use of linear transducers or other electronic implant devices to measure tendon tension which can be used to drive actuation of a prosthesis. While the systems and methods are primarily described herein as they could be applied to a biointegrated prosthesis using osseointegration, the systems and methods may alternatively be applied to an artificially driven prosthesis using electricity, pneumatics, or any suitable external energy source. In some variations, the prosthesis of the systems and methods may not include biointegration but instead interface with one or more artificial driven source.

Figure 9A:
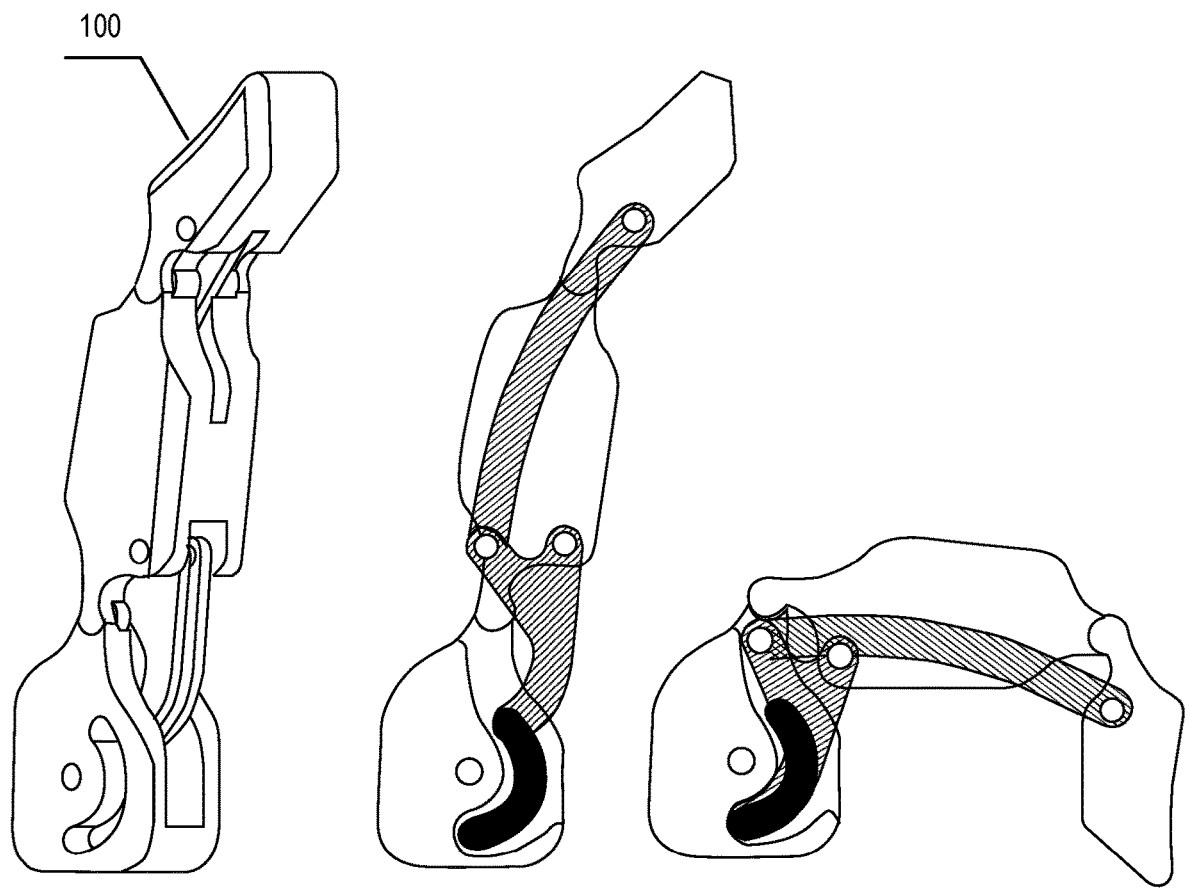
FIG. 9A is a set of schematic diagrams of a prosthesis with a linkage system variation that could couple to an artificial tendon system.
Figure 9B:
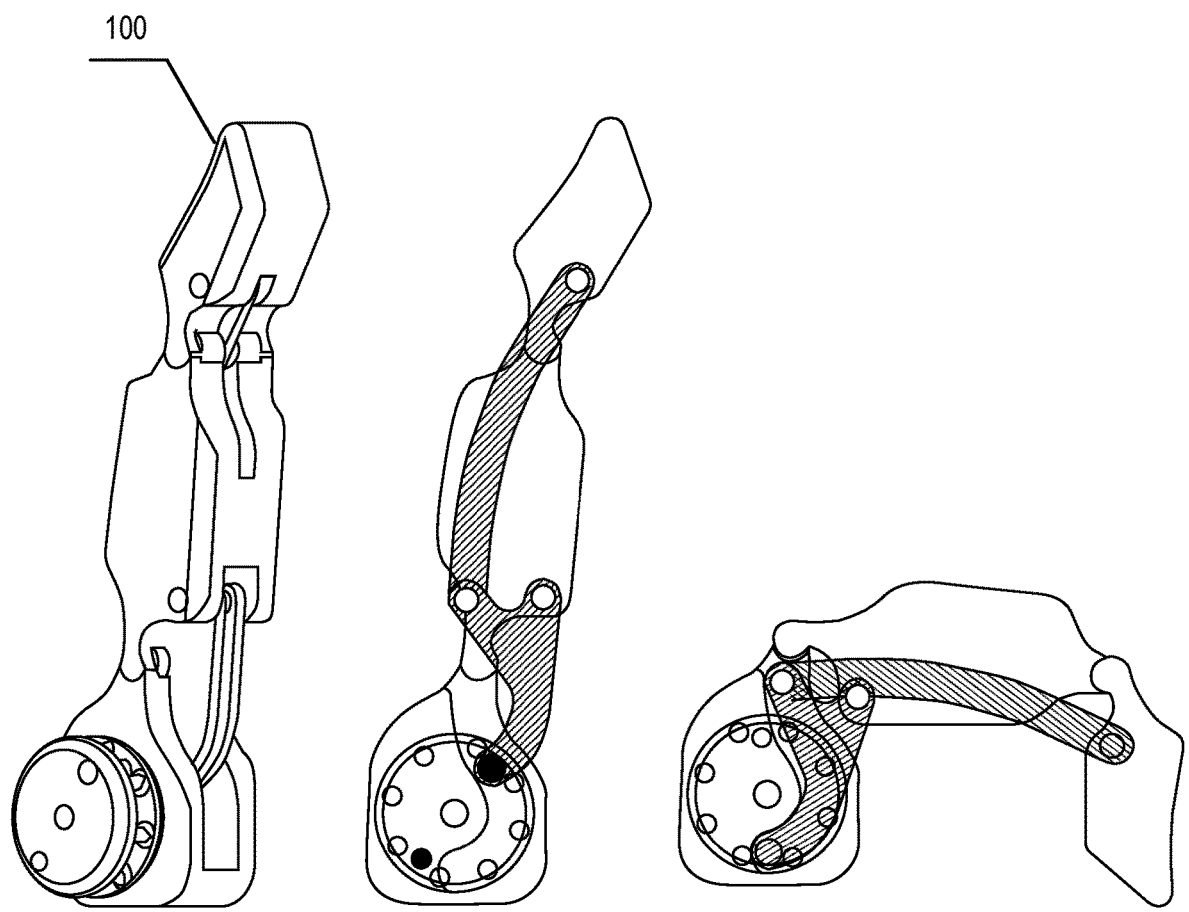
FIG. 9B is a set of schematic diagrams of a prosthesis with a linkage system variation using a pulley mechanism to couple to an artificial tendon system.

In some variations, the systems and methods may be a hybrid wherein actuation of the prosthesis may be partially tendon-actuated and partially artificially driven. In one variation, a first set of actuated actions (e.g., one or more such as actuation of joints A and B) may be tendon-actuated and a second set of actuated actions (e.g., one or more such as actuation of joints C and D) may be artificially driven. In another variation, one or more actions may use tendon/muscle-driven actuation in combination with artificially-driven actuation. For example, tendon actuation of an artificial tendon may be amplified through a coupling mechanism with a motor-driven actuator. As yet another variation, the systems and methods may use an AT to integrate with a linkage system of a prosthesis (e.g., a four-bar linkage system incorporating a compliant joint) as shown in FIG. 9A. As shown in FIG. 9B, a pulley mechanism or other coupling mechanism may be used to integrate an artificial tendon system as an input to a linkage system.

Figure 2A:
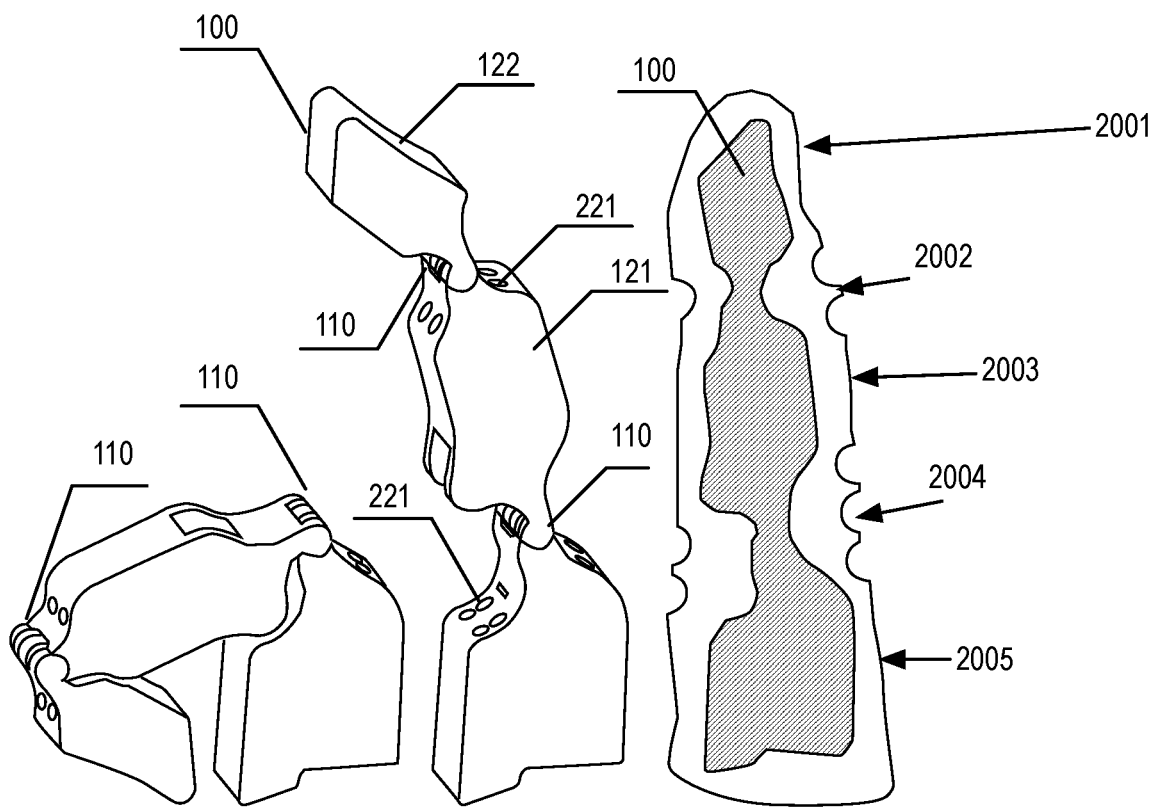
FIGS. 2A-2C are schematic representations of exemplary systems for an articulating finger prosthesis with identification of the distal phalanx 2001, distal interphalangeal joint (DIP) 2002, middle phalanx 2003, proximal interphalangeal joint (PIP) 2004, proximal phalanx 2005, flexor digitorum profundus (FDP) 2006, flexor digitorum superficialis (FDS) 2007, long extensor central band 2008, and long extensor lateral band 2009.
Figure 2B:
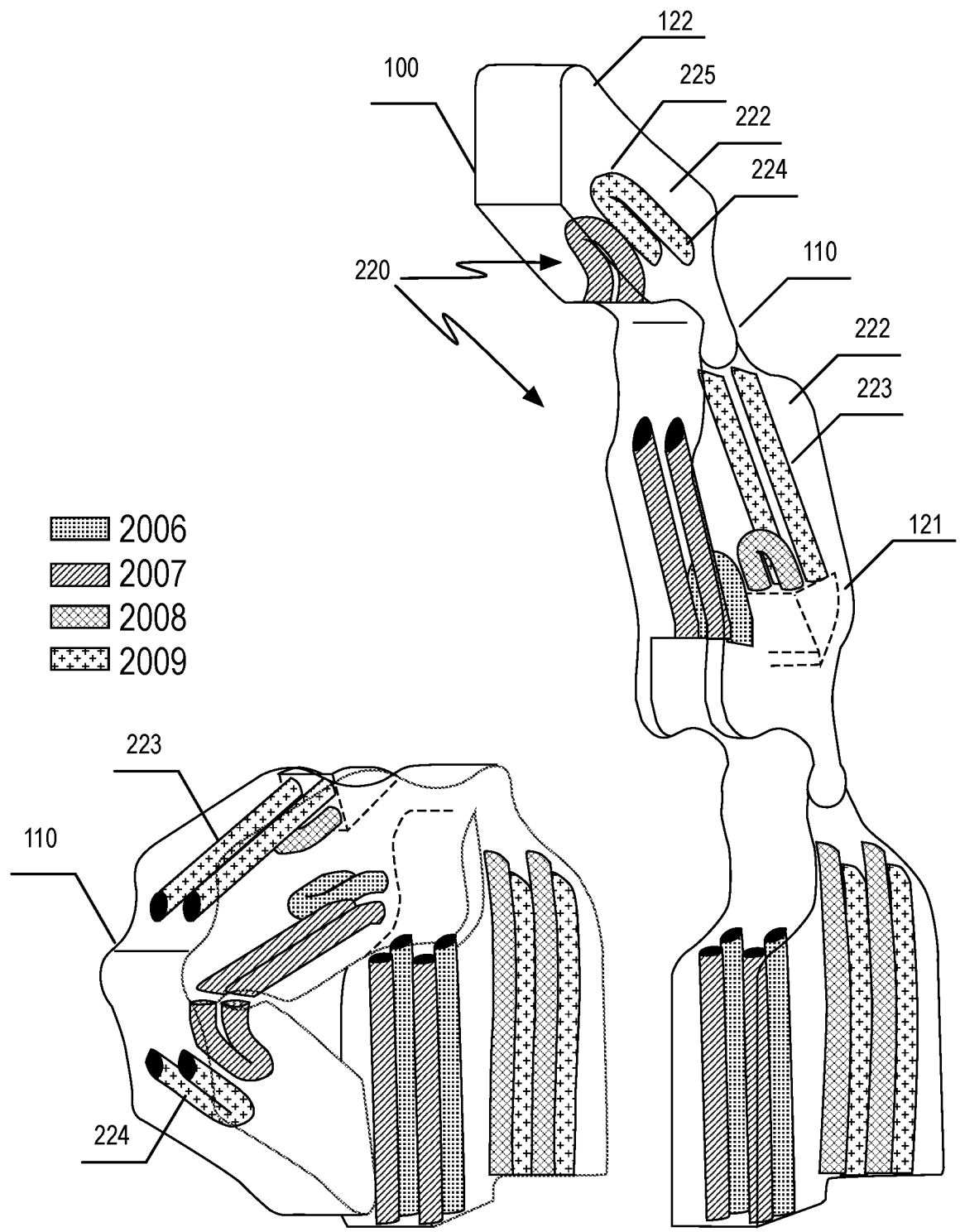
Figure 2C:
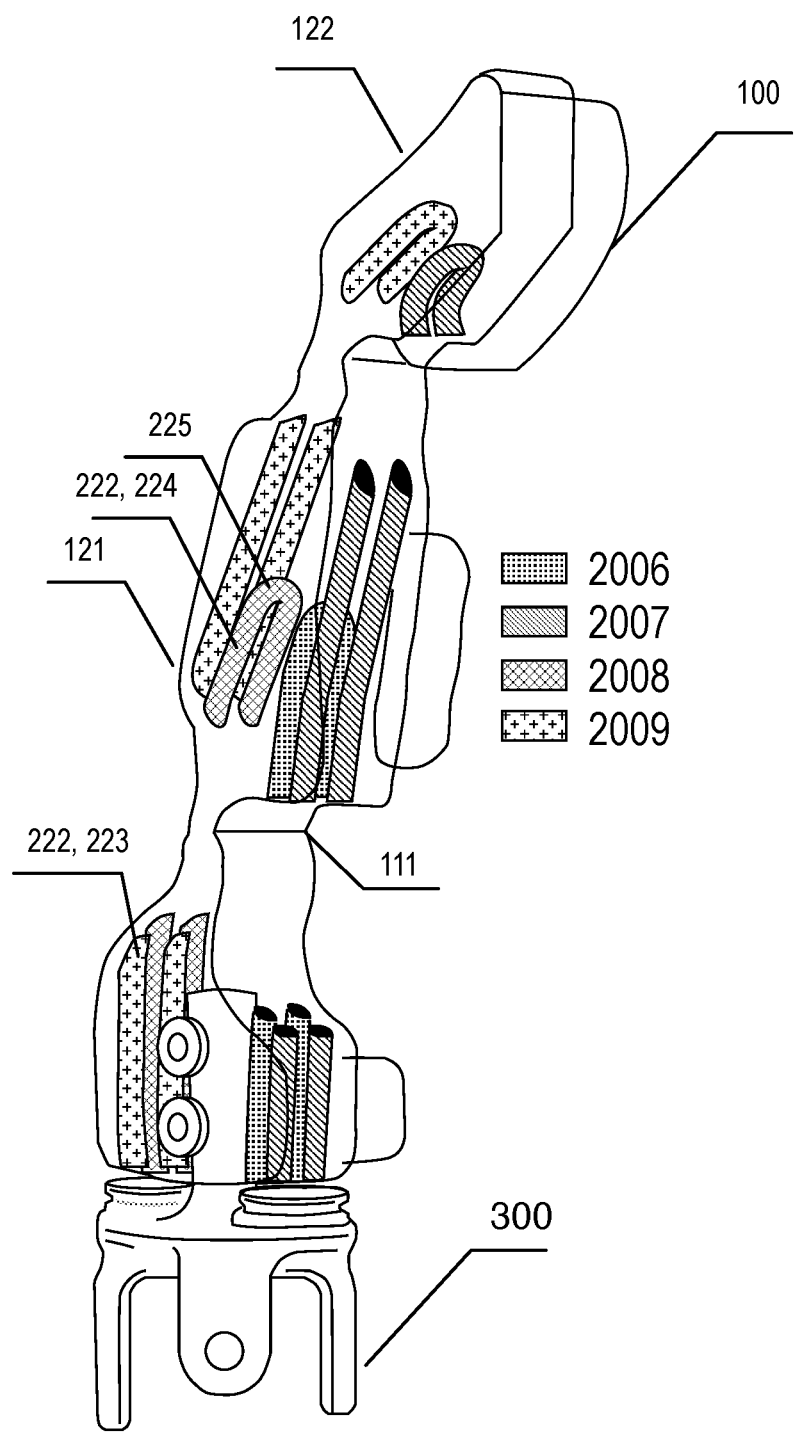
Figure 3A:
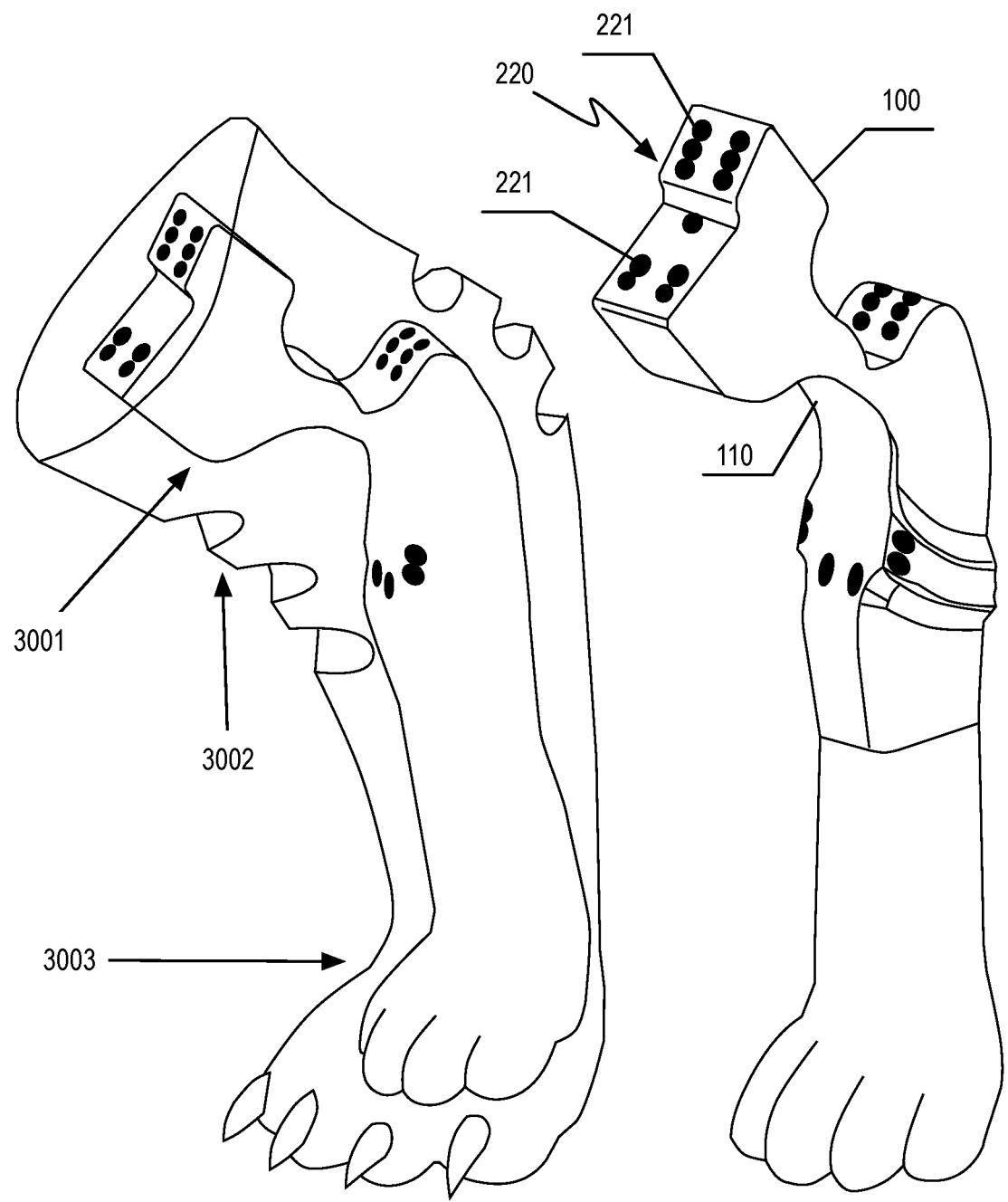
FIGS. 3A-3B are schematic representations of exemplary systems for an articulating hindlimb prosthesis with identification of the tibia 3001, calcaneal joint 3002, pes 3003, superficial digital flexor 3004, gastrocnemius 3005, common calcaneal 3006, peroneus longus 3007, long digital extensor 3008, and cranialis tibialis 3009.
Figure 3B:
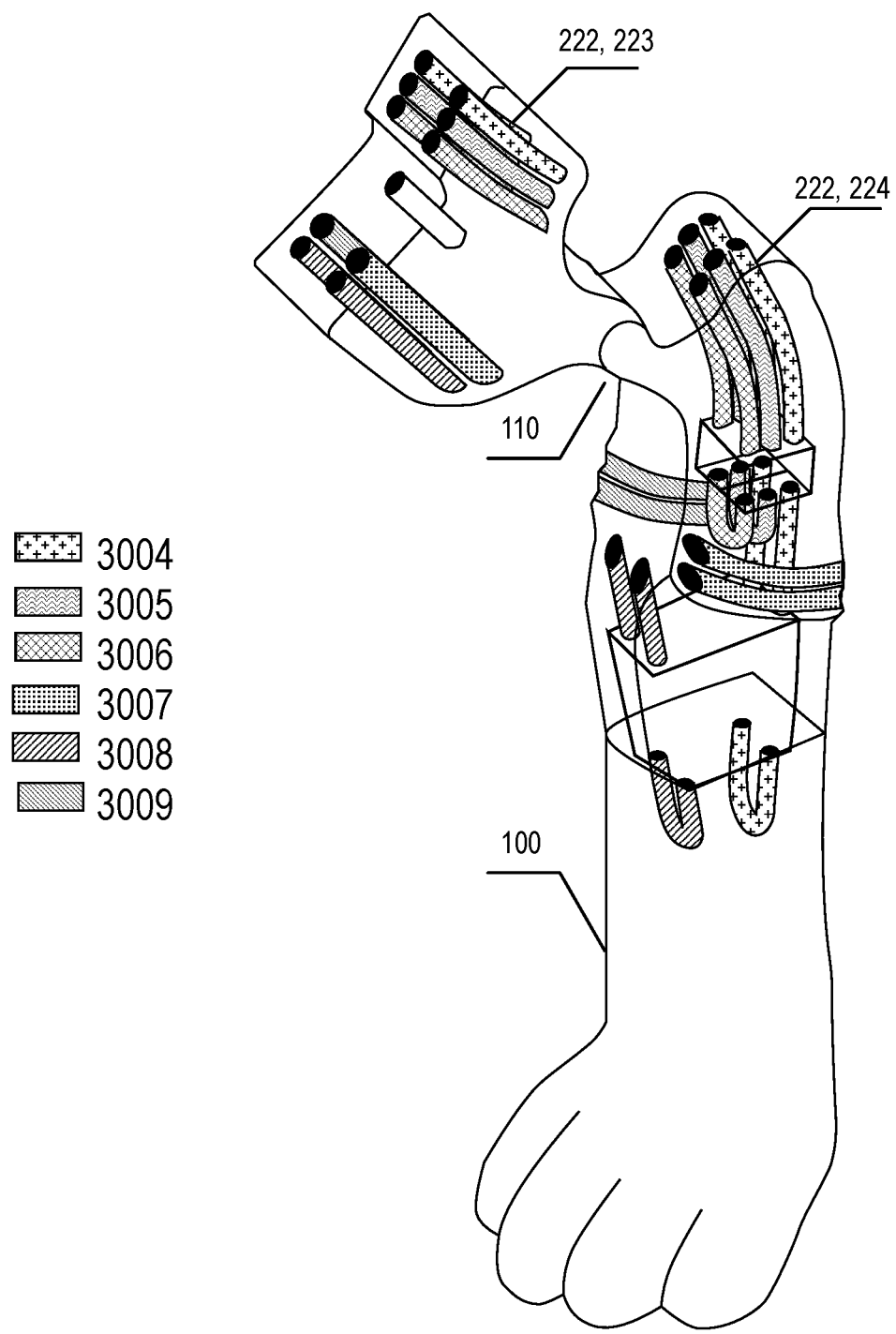

The systems and methods can be used in a variety of types of actuating prostheses. As one particular example, the systems and methods can be used for partial, single, or multiple finger amputees (e.g., as shown in FIGS. 2A, 2B, 2C). As another example, the systems and methods may be used for animal limb amputees (e.g., as shown in FIGS. 3A and 3B). Herein, a finger prosthesis and a hindlimb of an animal (e.g., dog) may be used as way of example. However, the systems and methods are not limited to only these types of prostheses. The systems and methods may be used for arm, hand, finger, leg, foot, toe, and/or other forms of amputations. In such examples, the systems and methods may be used for an accurate anthropometric prosthesis (e.g., dimensions of the prosthesis matching or approximating dimensions of a human user), but the systems and methods are not limited to directly imitating a body part. For example, the systems and methods may be used to biologically actuate an attached non-anthropomorphic prosthesis (e.g., a device not resembling that of a human), like an electromechanical gripper or mechanical object.

The systems and methods with biointegration may be used by having a user undergo a surgical procedure to implant an AT system and an osseointegration abutment 300. Such a procedure may be performed as a single 2-stage surgery, for example. The surgical procedure(s), in some variations, would involve attaching the AT system implanting the osseointegration (OI) abutment, and constructing or otherwise establishing the infection mitigation system. Once the AT system has successfully tissue-integrated with the existing tendon or muscle, the abutment has sufficiently osseointegrated, and the infection mitigation system has been properly integrated with the OI abutment, the prosthesis (e.g., a prosthetic finger) can then be attached.

The unique design of the systems and methods can adapt for a diversity of amputations (e.g., across any finger or phalanx) and can be configured for different situations. Accordingly, the biointegration of the AT system may be adapted to a variety of situations and conditions. In one example, if tendinosis is present in the residual tendons, the AT system may be attached to the forearm muscle corresponding to the phalanges of interest. In another example, if tendinosis is not present, the ATS may be attached directly to the residual tendons just proximal to the transverse carpal ligament.

The systems and methods can be adapted and configured to function across a variety of types of amputations. Furthermore, the systems and methods in some variations, can incorporate flexible manufacturability so that additive and customized manufacturing can adapt to unique properties of an individual. Accordingly, the systems and methods may be used in integrating with different residual flexor and/or extensor tendons (e.g., residual flexor digitorum profundus tendon).

The systems and methods enable musculoskeletal integration that can avoid and/or mitigate biological risks. For example, the systems and methods may avoid excessive movement of the skin at the skin-abutment/tendon interface, thereby avoiding or mitigating risk of breakdown. As another example, the systems and methods disclose a variety of solutions whereby the interface between internal and external environments is protected.

The systems and methods described herein can address multiple challenges to achieve an artificial tendon-driven prosthesis.

As one example, the systems and methods may establish an accurate and natural translation between biomechanical actuation and prosthesis actuation. This can involve designing parameters of the systems and methods for a biomechanically accurate range of motion and actuation strength (e.g., grip strength in the case of prosthetic hand/finger).

The systems and methods, in some variations, may apply a biomechanical model that relates the body weight of the specimen and the dimensions of the sound limb to the tendon moment arm and joint stiffness of a prosthetic bone to match expected mechanics to mechanics when used by a patient. This model may be used to enable attaining a biomechanically accurate range of motion and actuation strength (e.g., grip strength for a hand or finger prosthesis) in the prosthesis per patient.

Furthermore, systems and methods can be scalable in design such that the system could be scaled and customized. The systems and methods may employ unique joint designs (e.g., application of compliant joints), tendon channeling through the prosthesis, mechanical modeling, additive manufacturing and other rapid manufacturing or other techniques for part customization, and/or other approaches to calibrate the prosthesis for natural use.

In the application of the systems and methods to a hand or finger prosthesis for example, a finger prosthesis may be scaled to fit the anatomy of the human finger. The prosthesis of the systems and methods may include a compliant joint (i.e., a "living hinge" design), which may include elements of the compliant joint disclosed in US Patent Application with Publication No. US 2019/0328550, filed 29 Apr. 2019, and titled "A COMPLIANT FOUR-BAR LINKAGE MECHANISM FOR A ROBOTIC FINGER", which is hereby incorporated in its entirety by this reference, which is hereby incorporated in its entirety by this reference.

The compliant joint prosthesis may include at least two materials: one rigid piece centrally located and discontinuous at the joint, and two flexible continuous lateral bands simulating "ligaments". This design allows the same range of motion (ROM) of a hinge joint while providing the bones a shock-absorbing capacity to withstand high shear loading indicative of blunt forces to the finger. A network of four channels (220) may be cut or formed into the prosthetic bones to incorporate the artificial tendons and accommodate the flexor/extensor tendons, such as shown in FIG. 2B. As another exemplary variation, this may alternatively be implemented with a network of two channels 220): one flexor and one extensor tendon integration). Other suitable configuration of AT integrations may alternatively be used to adjust to other joints of interest for a human or animal. In some variations, an external AT segment loops about an actuation point. The location of the loops within the prosthetic bones may be anatomically accurate with respect to each tendon's tendon-to-bone insertion point. Each artificial tendon, in some variations, can loop through its designated channel so both ends of the tendons can be attached to the residual tendons through a system for mitigating infection. Alternative variations could alternatively be terminated or otherwise attached/fixtured at distal point. As such an exemplary variation, an artificial tendon segment could be knotted, crimped, or otherwise attached at its most distal point within a pone at its designated tendon-to-bone insertion point.

The tendon force required for finger motion can be dependent on the size of the tendon, stiffness of the joints, and the friction of the tendon against the surrounding tissues. Similarly, the prosthetic joint torque can be directly related to the anthropometric dimensions of the finger bones, moment arm between tendon and point of joint articulation, and resistance of the joint to bending. While natural joint resistance in-vivo can be attributed to the surrounding tissues, in the prosthesis the systems and methods may be configured to control joint resistance and/or other mechanics of the artificial tendon by varying the thickness of flexible material at each hinge and varying other parameters of how the artificial tendon interfaces with the actuation point and the prosthesis.

Modeled natural joint resistance of a natural body can be applied such that prosthesis design can be evaluated and modeled virtually and then used in directing manufacturing and production. The models can be used to output desired torque given anthropometric measurements and body weight of a specific subject, allowing configuration of stiffness of a prosthetic joint to replicate unique joint biomechanics.

Figure 6:
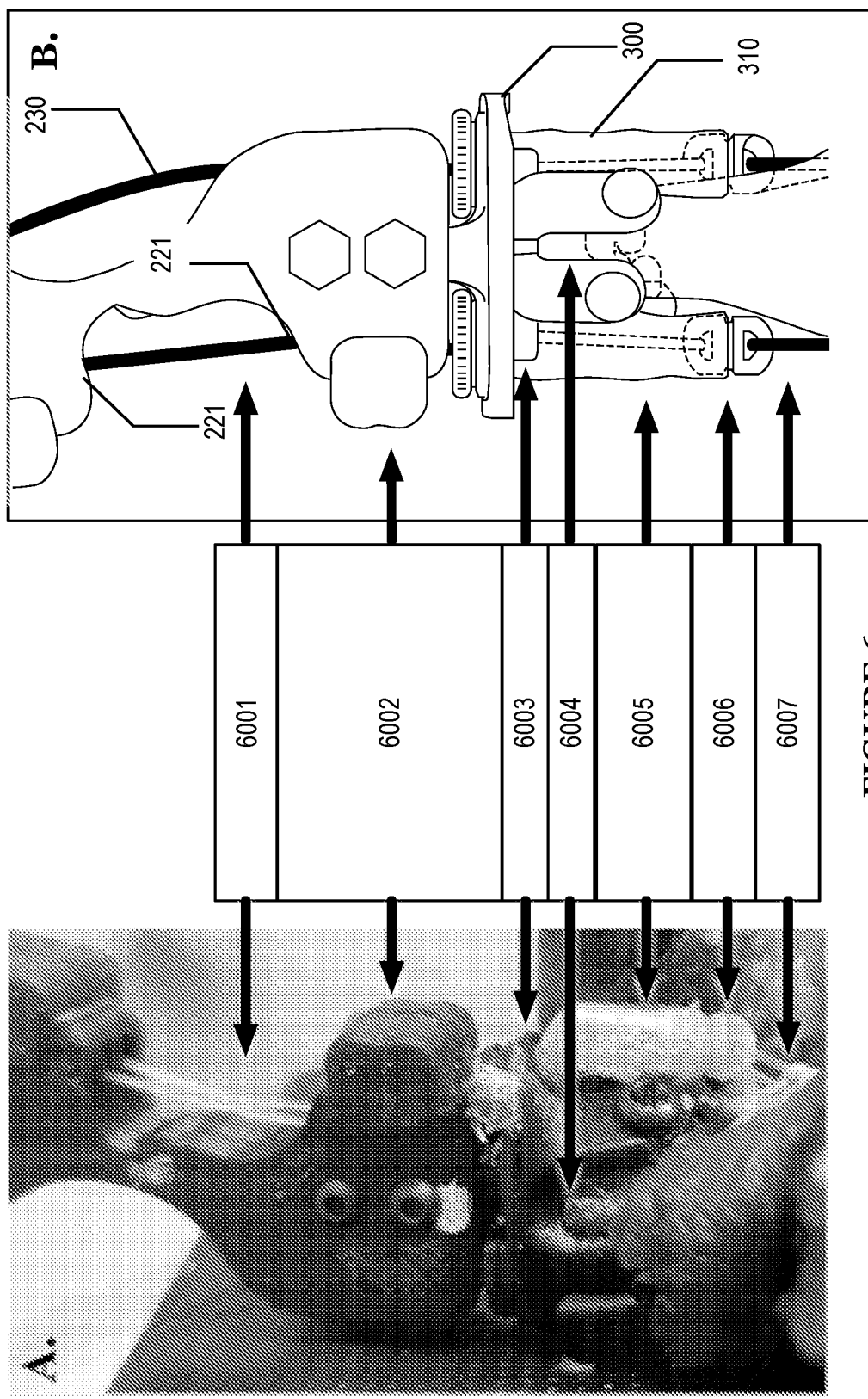
FIG. 6 shows one variation of a tendon interface that incorporates two tendon attachment discs with a sealed flexible film pocket with indication of the external artificial tendon 6001, prosthetic proximal phalanx 6002, osseointegration abutment 6003, residual proximal phalanx 6004, sealed flexible film pocket 6005, tendon attachment disc 6006, and internal artificial tendon 6007.

Additionally, as a biointegrated prosthesis, the systems and methods may also address mechanical properties of a used AT system and OI abutment. As one example, the systems and methods may be used for a prosthetic finger which may simulate actuation of one or more joints of a finger (e.g., a proximal interphalangeal (PIP) and/or a distal interphalangeal (DIP) joint) and integration with a finger flexor or extension tendon (e.g., flexor digitorum profundus (FDP)). The prosthesis system may be connected to a residual bone using an OI abutment, which may make use of a tripod titanium mini-plate for an osseointegrated digit prosthesis or a quadrupod design as shown in FIG. 6. The mini-plate anchored into the distal end of the residual finger through three equidistant axes with 1.5 mm mini-plates and screws. This construction may be used to make a more stable implant concerning lateral torque movements and prevent loosening during insertion/removal of the prosthetic finger. The absence of an intramedullary component may also mean that stress within the phalanx is decreased over time, which may prevent or mitigate occurrences of fractures/weakening of the residual bone which would compromise prosthesis integrity. An abutment of the systems and methods may be modified to accommodate the loading conditions of the prosthesis and further improve fixation to the bone. In some variations, the abutment of the systems and methods may feature a quadrupod design with each anchoring screw attached to the bone at different depths from the amputation site (e.g., 5, 6, 7, and 8 mm but may be configured for type of amputation and/or patient) to prevent bone fracturing. The abutment may also be designed to accommodate the ATS and infection mitigation system through two ports cut into the OI abutment base. The abutment may be designed to use the 1.5 mm of cortical bone around the finger perimeter for fixation, since finger bones lack the necessary amount of usable space within the intramedullary canal to use conventional OI methods. By using this method for fixation, the OI abutment may have the capacity to be used by all finger amputees irrespective of amputation site across any phalanx.

An OI abutment may be attached using screws or other attachment fasteners, which may be configured to prevent stress shielding for both compressive and tensile loading, properly distributing force between the implant and bone interface (e.g., to avoid bone resorption and/or improper bone remodeling). Finite Element Analysis may be used to characterize the optimal screw orientation, location, and configuration of attachment points. In one variation, the screws may be oriented at a determined angle (e.g., 30°-90° such as 45°) with respect to the axis of loading (e.g., two pointing proximally for compressive forces and two pointing distally for tensile forces).

As another alternative used for some forms of amputations, the OI abutment of the systems and methods may alternatively incorporate lower extremity OI techniques utilizing an intramedullary canal screw or press-fit design.

In some variations, additional or alternative components to the OI abutment may be used. In one exemplary variation, a hybrid design variation may incorporate a partial intramedullary component in conjunction with the OI abutment. For example, traditional a hybrid design integrating the OI abutment with a screw or press fit intramedullary component (of arbitrary length) could, in some variations, be used.

As another example of a challenge addressed, the systems and methods may provide effective infection mitigation mechanisms at the site that the artificial tendons interface between the internal and external environments of the body.

In one variation, the systems and methods may adapt a multifilament stainless steel cable crimp approach. A disc used with or as OI abutment may have two connection points, an internal connection to the artificial tendon and an external connection to the prosthesis. Fastened around the disc may be a non-porous material that extends distally to the external port of the OI abutment. The material may be secured, which functions to create a seal around both the disc and OI abutment, thus creating a pocket within the finger. The length of this pocket may be approximately 1.5-2 cm in length to accommodate the necessary tendon excursion for normal finger ROM. One knowledgeable in the art would appreciate that such values may vary and could depend on different tendon actuation lengths. In some variations, the pocket (e.g., a sealed flexible film pocket) could additionally extend through the metacarpals and into the forearm region. The skin at the amputation site can be sutured around the external circumference of the OI abutment and left to heal. This system variation can create two ports into the human body without risk of infection due to a non-porous, impermeable layer of material. This approach may accomplish normal joint range of motion by transferring internal tendon actuation to external tendon translation. Thus, the systems and methods may offer full (or large) range of motion while sealing the amputation site to mitigate risk of infection.

The systems and methods may provide a number of potential benefits. The systems and methods are not limited to always providing such benefits and are presented only as exemplary representations for how the systems and methods may be put to use. The list of benefits is not intended to be exhaustive and other benefits may additionally or alternatively exist.

As one potential benefit, the systems and methods enable a biomechanically accurate prosthesis where actuation of the prosthesis may map in a substantially 1:1 (i.e., one-to-one) manner to biologically controlled input. In other words, the flexing and extending of the body are reflected in substantially corresponding movement and forces in the prosthesis. This may result in a prosthesis with identical or similar range of motion. This may additionally result in effective strength of the prosthesis corresponding to similar levels of strength for a given level of body input/exertion.

As a related potential benefit, the systems and methods can enable a prosthesis with true proprioception (or at least high levels of proprioception). Proprioception allows a person to know the position and movement of their body at any given time. Enabling proprioception in a prosthesis can enable capabilities to perform highly dexterous movements. This may ensure an amputee can use their prosthesis in substantially the same way as their own limb.

As another potential benefit, the systems and methods may enable a type of prosthesis that can be used on a wide variety of types of amputations. For example, the systems and methods can be usable for amputees with or without an intact joint proximal to the site of the amputation.

Figure 4:
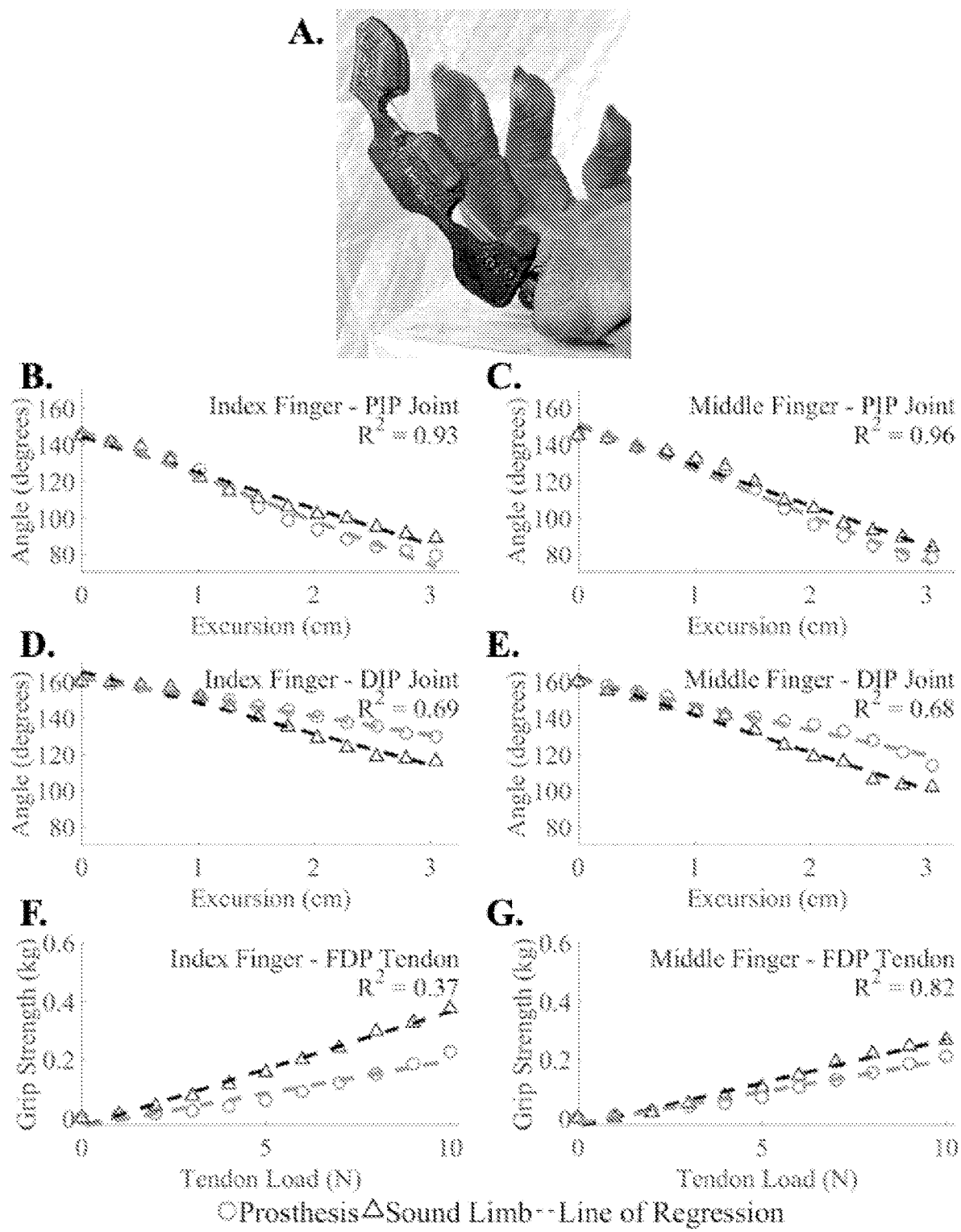
FIGS. 4 and 5 shows performance metrics of various exemplary system variations.
Figure 5:
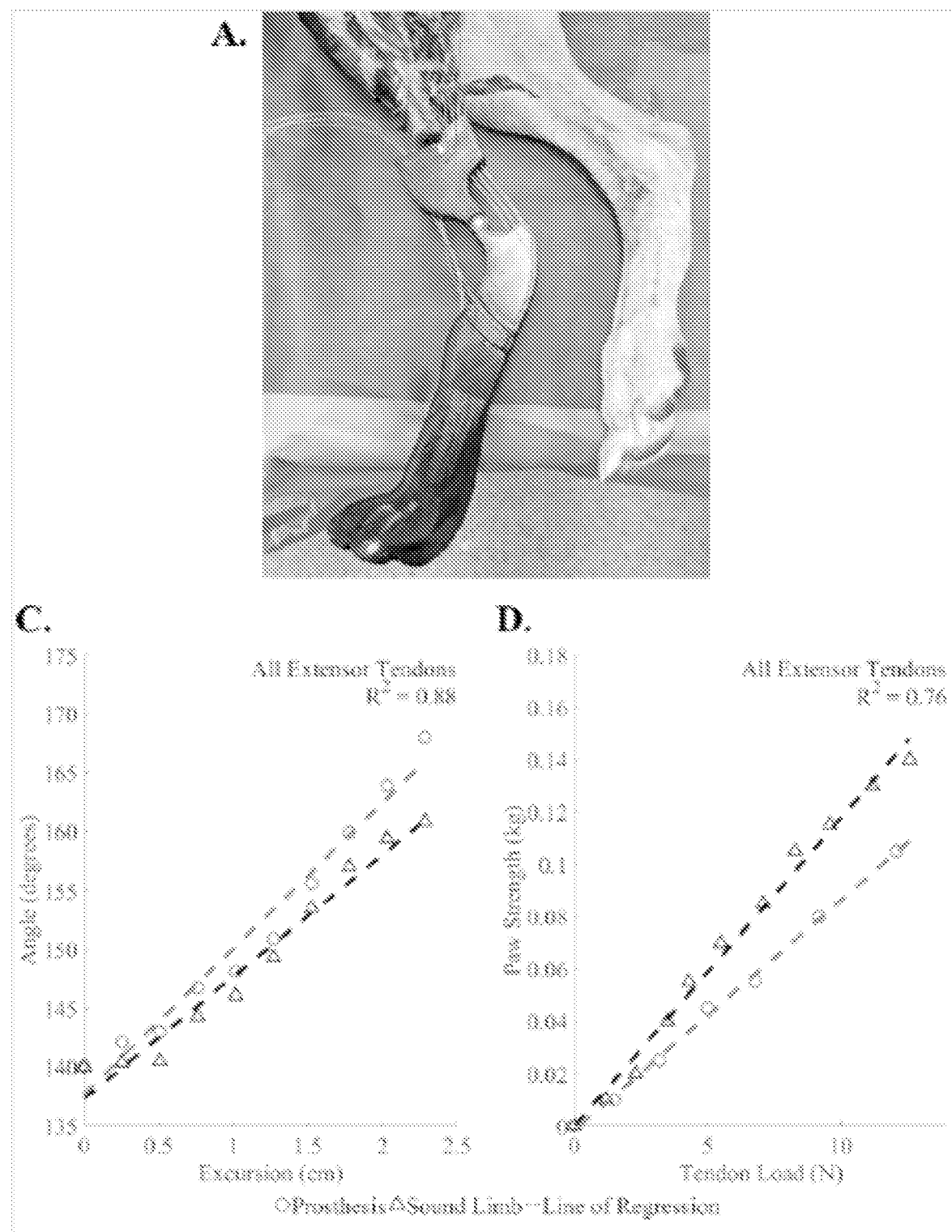

As another potential benefit, the systems and methods may enable a prosthesis that provides prosthesis actuation results that are similar to that of sound limb. In experimental analysis of some variations of the system and method, joint actuation and grip strength were observed to be able to achieve high R-squared values when compared to a sound limb. A series of experiments were performed to compare performance of a sound limb to that of a prosthesis applying the artificial tendon systems of the systems and methods. In such experiments, an increasing tensile force can be applied to a tendon, articulating a specimen's finger. The joint angles/grip strength were measured and compared to sound limb excursion. As shown in FIG. 4, experiments B, D, and F for a human index finger and experiments C, E and G for a human middle finger showed a high R-squared values in the range of motion indicating a strong fit between the prosthesis of the system and method and that of a sound limb. As shown in FIG. 5, similar high R-squared were also found in experiments in a canine hind leg prosthesis design using the AT systems of the systems and methods.

As another potential benefit, the systems and methods may be customizable to individual users, adapting to the unique nature of a user's amputation. In some variations, the prosthesis (or portions) may be 3D printed and modified to adjust the mechanical design of the integration of the artificial tendons and the actuation of the prosthesis. The abutment can similarly be casted, molded, machined, and/or otherwise manufactured to adjust for the integration of the artificial tendons, actuation of the prosthesis and an infection mitigation system.

As another potential benefit, the systems and methods may be tendon or muscle driven, utilizing natural articulation by the user. This may result in a more natural use of prosthesis by a patient.

As a potential benefit related to the tendon/muscle-driven potential, the systems and methods may have no dependence on an external power source. By being driven directly by the user, the prosthesis may effectively have a limitless window of use. In contrast, battery powered actuated prostheses have to be recharged periodically. While some variations may make use of a battery or power source, some variations can be fully mechanical, wherein the prosthesis only makes use of input from physical actuation by the user.

As another potential benefit, the systems and methods can be very maintainable. The systems and methods may not have any electronic components, which can be prone to breaking or needing repair. In some preferred variations, the prosthesis can be simple in construction and modular in design. If a piece of the prosthesis breaks, the design of the prosthesis can be such that the user can troubleshoot or fix without needing a technician.

2. System

As shown in FIG. 1A, a system for an artificial tendon or muscle driven prostheses can include an articulating prosthesis 100 and an artificial tendon (AT) system 200, wherein the artificial tendon system 200 is integrated with the articulating prosthesis 100 and coupled to a musculoskeletal system of a user. The system can additionally include an osseointegration abutment 300. The artificial tendon system can include an external tendon actuation interface 210 coupled to an actuation point 110 of the articulating prosthesis 100, through an osseointegration abutment 300, to a musculoskeletal integrated artificial tendon 230. The system functions as an actuating artificial appendage that is driven at least in part by natural human manipulation. Preferably, the actuation has direct proprioceptive feedback between musculoskeletal manipulation and the actuation of a prosthesis.

In particular, the system can be used to make a multiarticulated prosthetic finger and/or hand. The system may alternatively be applied to the creation of other types of prostheses such as arm, leg, foot, toe, and/or other forms of amputations.

As one exemplary variation, a system for a prosthesis may include an articulating prosthesis 100 with a set of actuation points 110; an artificial tendon system 200, the artificial tendon system being integrated with the articulating prosthesis 100 and include an external tendon actuation interface 210 coupled relative to at least one actuation point of the set of actuation points 110, and the artificial tendon system 200 also including integration with a musculoskeletal-integrated internal artificial tendon; and an osseointegration abutment 300 through which the artificial tendon system 200 couples the external tendon actuation interface 210 to the musculoskeletal-integrated internal artificial tendon integration 230.

In such variations, the artificial tendon system 200 includes or integrates with at least one artificial tendon that mechanically couples the articulating prosthesis 100 and one or more controlled portions of the user's body. The external tendon actuation interface will, in some variations, include or be an external AT segment. The internal tendon actuation interface includes or is an internal AT segment. The external AT actuation segment connects or otherwise physically interfaces with the internal AT segment. In some variations, the artificial tendon system 200 will include or have integration with a plurality of ATs, wherein each AT includes an internal tendon segment and an external tendon segment. In a similar manner, a system including an articulating prosthesis 100 with integration with biointegrated ATs, the artificial tendon system 200 may include a plurality of artificial tendons that each include an external tendon segment configured to couple to an internal tendon segment through the osseoinduction abutment interface.

As described herein, different types of actuations may be enabled through the articulating prosthesis. The articulating prosthesis could have the external tendon actuation interface that couples relative to a single actuation point or, as an alternative variation, routes around multiple actuation points for actuation of multiple points.

Being coupled relative to an actuation point characterizes the tendon actuation interface connecting or otherwise engaging with the articulating prosthesis in a way whereby actuation of the AT can result in actuation of the actuation point.

In some variations, the osseointegration abutment includes an interface with tendon passthrough actuation. Tendon passthrough actuation characterizes a mechanism by which an artificial tendon system has an internally biointegrated AT have mechanical coupling to an external AT (which will preferably be integrated with the articulating prosthesis 100. In tendon passthrough actuation of an artificial tendon system that includes an internal AT segment and an external AT segment, actuation of an internal AT segment may correspond to proportional actuation of an external AT segment, with the actuation occurring relative to the abutment interface 300 (e.g., the abutment 300 is stationary on the body, while the AT(s) can slide back and forth with at least one degree of freedom through the internal-external interface). The osseointegration abutment accordingly may be decoupled from an AT (e.g., AT passes back and forth through the osseointegration abutment 300 without limits for a configured range of motion) or be non-rigidly coupled (e.g., actuation can still occur but with potentially one or more AT segments attached to a non-rigid element of the abutment 300). Various approaches may be applied to the osseointegration abutment 300 as described herein.

Figure 1B:
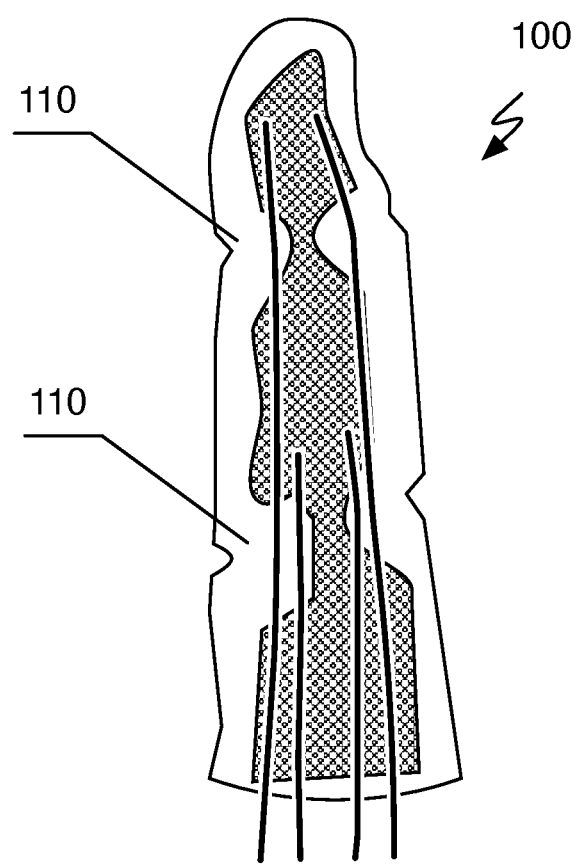
FIG. 1B is a schematic representation of a system variation of an articulating prosthesis.
Figure 1C:
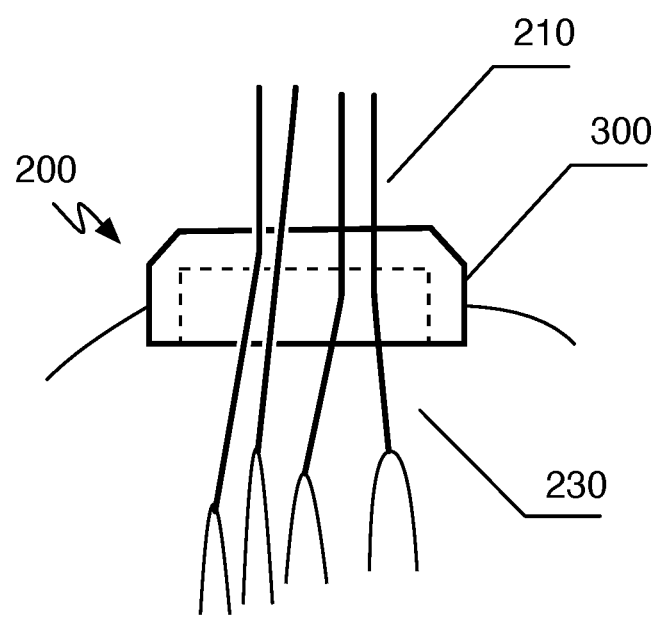
FIG. 1C is a schematic representation of a system variation of an artificial tendon system.

In some variations, the system can include the articulating prosthesis 100 integrated with the artificial tendon system 200. In one alternative embodiment, a system may include the artificial tendon system 200 as described herein with integration with a suitable articulating prosthesis 100. The articulating prosthesis 100 could include the prosthesis system described herein but may alternatively include another type of prosthesis or element to engage with an AT of the artificial tendon system 200. As shown in FIG. 1C, an artificial tendon system 200 variation may include an external tendon actuation interface 210; integration with a musculoskeletal-integrated internal artificial tendon; and an osseointegration abutment 300 through which the artificial tendon system 200 couples the external tendon actuation interface 210 to the musculoskeletal-integrated internal artificial tendon integration 230. The external tendon actuation interface 210 can couple to any suitable external component such as an articulating prosthesis. This variation may function to enable an artificial tendon system whereby an external system can be driven based at least in part on an artificial tendon that is musculoskeletal integrated. Any of the variations described herein relating to the artificial tendon system 200 may be adapted and applied to a system that includes the artificial tendon system 200 independent of or used in combination with a prosthesis.

In one alternative embodiment, a system may include the articulating prosthesis 100, which may be configured to interface with a suitable artificial tendon system or other type of drive system. The suitable artificial tendon system may be a variation of the artificial tendon system 200 as described herein but may alternatively be another suitable type of artificial tendon system. As shown in FIG. 1B, a tendon-driven (and/or muscle driven) prosthesis may include an articulating prosthesis 100 with a set of actuation points that engage with or includes an external tendon actuation interface, by which the prosthesis can be actuated at least in part with tendon/muscle-driven control. This function can enable a prosthesis with design characteristics that result in enhanced capabilities when used with a tendon-based drive system like the artificial tendon system 200 described herein. As one example, some design variations of the prosthesis may enable use of rapid manufacturing techniques, which in turn can enable calibration of prosthetic design to an individual (e.g., adjusting sizing, strength profiles, etc.). Any of the variations described herein relating to the articulating prosthesis 100 may be adapted and applied to a system that includes an articulating prosthesis 100 independent of or used in combination with a tendon tendon/muscle-drive system.

The system may be adapted to a variety of types of amputations and/or amputation conditions. Hand and/or finger prostheses are used as examples herein, but the systems and methods may be used in other types of prostheses such as arm, hand, finger, leg, foot, toe, and/or other forms of amputations. As one example, a system variation for a tendon tendon/muscle-driven hand or finger prosthesis may includes: a) a prosthetic finger with a body structure including a first actuation point, a set of tendon routing channels (220) through the body structure, the set of routing channels (220) comprising pairs of channels (222) in a proximal segment (223) before the first actuation point and in a distal segment (224) after the first actuation point; b) wherein the first actuation point is a compliant joint in the prosthetic finger with a flexible material formed at the actuation point; and d) an artificial tendon system 200 that includes a first external tendon segment (230) that is routed through a first side of the pairs of channels (222) loops back at or after the first actuation point (225) and is routed through a second side of the pairs of channels (222) as shown in examples of FIGS. 2A, 2B, 3A, and 3B. As another variation, the external AT segments may be represented and/or function as linkages of a mechanical linkage system of the prosthesis. For example, an external AT segment could be or actuate a linkage arm that functions as an input linkage to drive actuation of a linkage system (e.g., used to actuate a grasping motion of a finger). As described herein, with regard to compliant joints, the compliant joint may include rigid structures restricting and/or guiding range of motion and degrees of freedom in the compliant joint, and a flexible material for a restorative force. For example, the body could include a proximal rigid structure connected through a living hinge with flexible material to a distal rigid structure.

The articulating prosthesis 100 functions as the external artificial appendage which generally serves to take the place of a missing body part.

In one variation, the articulating prosthesis 100 can be a prosthetic finger. The system may be used so that at least one aspect of the prosthetic finger can be actuated. In one variation, tendon/muscle-driven actuation uses a single artificial tendon to affect a grasping action of the finger. This may be where multiple joints or a single joint can be controlled by the single artificial tendon. For example, a single artificial tendon may be used in actuating prosthetic DIP and PIP joints of a finger. In another variation, tendon/muscle-driven actuation can use multiple artificial tendons (which may have independent musculoskeletal integration) to control two independent actuation points. For example, a first artificial tendon may be linked with the DIP joint, and a second artificial tendon may be linked with the PIP joint. This integration can be used to enable extension of the finger (and similarly applied to the hand as well).

In another variation, the articulating prosthesis 100 may be adapted to a particular condition of the patient. In the case of a prosthetic finger, this may involve being a partial finger prosthesis and/or being a multi-finger prosthesis.

In one variation, the articulating prosthesis 100 can be a prosthetic hand. The system may be used so that at least one aspect of the prosthetic hand can be actuated. In one variation, tendon/muscle-driven actuation may be used to affect a grasping action where multiple fingers are controlled in unison. In another variation, tendon/muscle-driven actuation may make use of a set independent artificial tendons such that individual fingers (or individual subsets of fingers) can be independently controlled for actuation. A hand prosthesis may make use of the different variations described above for the finger prosthesis. For example, a hand prosthesis may also enable multi-jointed finger actuation such as having actuation of DIP and POP joints in the fingers of a hand. A hand prosthesis may additionally or alternatively enable wrist actuation or other forms of actuation.

Other types or classes of prostheses may also incorporate the systems and variations described herein, including prostheses for arm, hand, finger, leg, foot, toe, and/or other forms of amputations.

The articulating prosthesis 100 includes a structural body made of one or more parts, which in combination form rigid, semirigid, and/or flexible portions of the articulating prosthesis 100. As described below, some variations may make use of a combination of rigid and flexible portions within the articulating prosthesis 100. In particular, one preferred variation of the articulating prosthesis 100 can include one that includes at least one compliant element or joint.

The articulating prosthesis 100 includes at least one actuating element. An articulating element of the articulating prosthesis 100 is referred herein as an actuation point 110. The actuation point may be a joint enabling actuation with at least one angular dimension such as a hinge joint (e.g., angular rotation in one dimension about a point), a pivot joint, a saddle joint, a ball-and-socket joint, ellipsoidal joint (e.g., joint simulating wrist-joint), and/or other types of joints. The actuation point may also be a multi-jointed actuation element wherein actuation is chained or linked or distributed across a region/element of the articulating prosthesis using a more complex mechanism (e.g., a series of connected jointed elements). The actuation point may additionally or alternatively include translational actuation along one or more dimensions or a path can be performed. For example, a linear actuation mechanism with a restorative source (e.g., spring of elastic material) may allow the tendon/muscle-driven actuation to effect or cause linear motion.

The articulating prosthesis 100 may alternatively include multiple actuation points 110. Accordingly, in some variations, the articulating prosthesis 100 can be multiarticulated, wherein the prosthesis includes multiple actuating joints as shown in FIG. 2A. However, in some variations, the articulating prosthesis 100 may have a single articulating joint. The articulation may occur through one or more mechanical mechanisms. In some variations, the articulating prosthesis 100 may include a compliant joint.

A compliant joint can include a rigid bone structure and at least one compliant flexible body structure such as in the systems and methods for a compliant four-bar linkage mechanism in US Patent Application with Publication No. US 2019/0328550, filed 29 Apr. 2019, and titled "A COMPLIANT FOUR-BAR LINKAGE MECHANISM FOR A ROBOTIC FINGER", which is hereby incorporated in its entirety by this reference. In some variations, described in more detail below, a rigid bone structure may be layered with a compliant flexible body structure. As one exemplary variation, the articulating prosthesis 100 can include a central rigid body structure with one or more flexible body elements on outer layers. The flexible outer layers may be molded around the central rigid body structure or combined in any suitable manner.

The articulating prosthesis 100 can include one or more actuation points 110 where an artificial tendon will interface and/or couple with the articulating prosthesis 100—where the external tendon actuation interface couples to the articulating prosthesis 100. The external AT segment will interface directly with the articulating prosthesis 100 and then also interface with an internal AT segment directly or with an interface to the internal AT segment. In some variations, the actuation points approximate the bone insertion points of the corresponding body part. Movement of an artificial tendon translates into actuation of at least one joint through the actuation point. In one variation, the artificial tendon may attach or be attached to the actuation point (e.g., terminated). In another variation, the artificial tendon may wrap around an actuation point that is formed as a channel or pulley. In some variations, the channel can be formed so that it compresses and applies a contractive force on multiple structural layers of the body. For example, in the variation with a central rigid body element with one or more flexible body elements on outer layers, the channel may be routed so that the artificial tendon pulls the layers together when actuated.

As stated, the articulating prosthesis 100 includes a set of actuation points 110. In one variation, the set of actuation points could be a single actuation point 110 which may be integrated with the artificial tendon system 200. In another variation, the set of actuation points 110 could include a plurality of actuation points 110 that are integrated with the artificial tendon system.

Variations with a plurality of actuation points 110 may use various configurations in the arrangement of actuation points 110, interaction between actuation points 110 (e.g., independent or linked), and/or shared or independent connections to ATs.

In a variation of a prosthetic finger with a plurality of actuation points 110, an external tendon actuation interface coupled relative to at least one actuation point of the set of actuation points can include a first external AT segment coupling relative to a DIP actuation point of the prosthetic finger and a second external AT coupling relative to a PIP actuation point of prosthetic finger. Here coupling can describe a physical attachment, anchoring, or otherwise mechanical interface whereby the actuation of the AT can actuate the actuation point. In such a variation, two ATs may be used so that the DIP and PIP joints of a finger can be directed by actuation of two different ATs.

In some variations, an AT may be coupled about multiple actuation points so that linked actuation of a plurality of actuation points can be affected by actuating the AT. As an alternative variation to the prosthetic finger above, a single AT may be coupled about two actuation points. In such a variation, an external tendon actuation interface coupled relative to at least one actuation point of the set of actuation points can include a first external AT segment coupling relative to a DIP actuation point of the prosthetic finger and additionally coupling relative to a PIP actuation point of prosthetic finger, which functions to cause linked actuation of the DIP and PIP actuation points.

In some variations, an AT may be used to actuate multiple distinct digits so that different substantially independent joints may be actuated by one AT. Accordingly, in some variations, an external tendon actuation interface coupled relative to at least one actuation point of the set of actuation points can include a first AT segment coupling relative to an actuation point of a first actuating digit of the articulating prosthesis and a second actuation point of a second actuating digit of the articulating prosthesis.

In another variation, multiple ATs may be used to actuate different digits of a prosthesis. Accordingly, in some variations, an external tendon actuation interface coupled relative to at least one actuation point of the set of actuation points can include a first AT segment coupling relative to an actuation point of a first actuating digit 121 of the articulating prosthesis and a second AT segment coupling relative to a second actuation point of a second actuating digit 122 of the articulating prosthesis.

The actuation points 110 and the design of actuating joints or degrees of freedom can be designed and optionally calibrated to a mechanical model for users. In some cases, such as where a prosthesis is custom made for a patient, the actuating points 110 can be custom calibrated for desired strength and range of motion for that patient. Rapid manufacturability of the articulating prosthesis 100 can enable such custom design.

The external AT segments may be routed through or on the prosthesis 100 and relative to the actuation points 110. For a given actuation point, an external AT segment can be coupled at a point of leverage to effect or cause actuation by the actuation point 110. In some variations, the actuating prosthesis 100 can include internal channels 221 through which the external AT segments may be routed. The articulating prosthesis 100 may function to encase, shield, and/or otherwise route or guide the artificial tendons. The channels 221 may be grooves along which the artificial tendons move. The channels 221 may alternatively be tubes or enclosed channels through which the artificial tendons can pass and move. In some variations, a channel 221 could be a pulley or rotational element to reduce friction and guide a tendon as it moves. Internal channels 221 (e.g., defined through cavities) can provide flexibility in defining mechanical actuation as well as securing/shielding the external AT segments.

In one variation, the system (e.g., the articulating prosthesis) can include, relative to an actuating point, a proximal channel 223 and distal channel 224, through which an external AT segment is routed as shown in example FIGS. 2A, 2B, 2C 3A, and 3B. The proximal channel 223 and distal channel 224 may be defined cavities or on or within the body of the articulating prosthesis 100. A corresponding external AT segment may thereby route from the osseointegration abutment through the proximal channel 223, about the actuating point and then through the distal channel 224. In some variations, the system or articulating prosthesis can include a continuous channel for the external AT segment.

In another variation, the system (e.g., the articulating prosthesis can include pairs of channels 222, wherein an external AT segment can be routed in a loop passing through adjacent sides of a pair of channels 222.

In one variation, the external AT segments may be terminated and fixtured (i.e., attached) on one end at or to the articulating prosthesis 100.

As another variation, the external AT segment may be routed through or otherwise couple to the articulating prosthesis 100 wherein the two ends of the AT segments terminate outside of the articulating prosthesis 100. For example, an AT segment may loop around a point on the articulating prosthesis 100 and then crimped or terminated near the osseointegration abutment 300. Looping may mitigate chance of mechanical failure. More specifically, the system may include a pair of channels defined in the articulating prosthesis 100 (e.g., in the body of the articulating prosthesis) and through which an external artificial tendon segment is routed through one side of the pair of channels, routed about an actuation point, and routed back through the opposing side of the pair of channels. The opposing ends of the external artificial tendon segment may be terminated at substantially the same site, though other termination approaches may alternatively be used.

As shown in the finger prosthesis of FIG. 2B and the hindlimb of FIG. 3B, parallel channels may be used running down the length of the prosthesis (e.g., or within select segments of the prosthesis) for routing of artificial tendon fibers and then at the actuation point, the channel can cross over to the other side. In variations of the articulating prosthesis 100 that employs a joint like the compliant joint, the channeling of the AT segment may apply a compressive force between an outer compliant material layer (shown as the semi-transparent elements of the prosthesis in the figures) and a rigid bone structure (shown as the solid dark element in the figures). This may also reduce the stress concentration on the artificial tendon fibers since no knotting or clamping exists. This can function to make the system more robust, reduce occurrences of failure, and/or extend how long the system may be used without maintenance.

In general, an AT segment coupled to the body will directly interface with a single actuation point. In some variations, an artificial tendon may interface with multiple actuation points. For example, this may function to translate movement of one AT to multiple artificial fingers. In another variation, this may function to translate movement of one AT to multiple actuation points of a prosthesis member, such as a finger. For example, one AT segment may couple with and actuate a DIP and a PIP joint of a finger prosthesis. In some alternative variations, multiple artificial tendons attached to distinct musculoskeletal elements can connect to one or more actuation points.

In one variation, the external AT segment could interface with a linkage system used in actuating one or more joints or actuation elements of the prosthesis. In the case of a compliant joint described herein, the external AT segment may couple to an input linkage of a four-bar linkage system formed through the compliant joint. In another variation, the external AT segment (or a portion of the eternal AT segment) could be a rigid or semi-rigid structure that could act directly as a linkage member of some linkage system. In the variation involving a compliant joint, another variation could have the external AT segment being or being coupled to the input linkage of a four-bar linkage system formed through the compliant joint.

In one linkage-based variation, a set of linkages could be coupled together and be responsible for finger motion. A four-bar linkage design (or other type of linkage design) using a compliant joint and/or another suitable joint could use the linkages to standardize the finger motion of the prosthesis thereby turning the tendons into a true actuation device. The linkages could be actuated from the AT system in place of an external actuation source like an electrically powered motor. In one variation, two flexible four-bar linkages can be combined or chained together. Other multi-stage linkage systems involving two or more linkages may be used. Such linkage systems may include compliant, flexible, and/or non-compliant joints. A multi-stage four bar linkage system can be made up of two or more flexible four-bar linkages with each linkage system being either crossing or non-crossing. As shown in an example of FIG. 9A, a distal linkage system may be a crossing flexible four-bar linkage system and the proximal linkage system may be a non-crossing flexible four-bar linkage system. To attach the tendons to the linkages, an external pulley can be used as shown in FIG. 9B, though other mechanical coupling mechanisms may alternatively be used. The pulley would mechanically connect to the tendons in one connection and the linkages in another connection. The flexor tendons would attach to said pulley on one side and the extensors on the other (e.g., at 9 and 3 o'clock if the pulley was a clock or alternatively described: at 90° and 270° if 0° is aligned toward distal end of the prosthesis). When the flexors actuate the pulley, the pulley would rotate and thus actuate the linkages to bend the finger. The linkages, being mechanically coupled therefore can be set to have a 'bending ratio' which can for instance equate 1 cm of flexor tendon excursion to full PIP and DIP rotation. The linkage coupling placement can also determine at which rate the DIP flexes with respect to the PIP. This is another potentially added benefit.

As described, in some variation, the articulating prosthesis 100 includes at least one compliant joint. A compliant joint includes at least one restorative element. The restorative element promotes a steady state actuation position of the articulating prosthesis 100. As described above, one exemplary variation, the articulating prosthesis 100 can include a central rigid body structure with one or more flexible body elements on outer layers. As another alternative, the articulating prosthesis 100 can include an external rigid body structure with internal flexible body elements connecting or bridging two rigid body structures. The flexible outer layers may be molded around the central rigid body structure, within the rigid body structure, and/or combined in any suitable manner. Alternative approaches may form the body of the compliant joint (or any suitable part of the prosthesis) as a single continuous piece. For example, a compliant joint may be 3D printed as a single, continuous piece.

A compliant flexible body structure of the articulating prosthesis 100 may enable some and/or all sections of the prosthesis to bend and/or deform due to an exerted force. In one variation, the compliance of the rigid bone structure is centralized into localized regions, wherein the compliant structure can serve more as a compliant joint or compliant joint region.

Preferably, a compliant joint can act as a living spring with a stable "resting" position that can deform along at least one degree of freedom, and then returns to a "resting" position once the force has been removed. The degree of freedom is preferably a rotational degree of freedom. The degree of freedom may alternatively be elastic longitudinal deformation (e.g., stretching or compression) or a combination. The compliant joint may additionally include multiple angular and/or translational degrees of freedom.

A compliant joint may function to provide a mechanism for planar actuation of a joint that applies a restorative force when actuated from a steady state position. More specifically, the compliant joint may function to convert pulling of an artificial tendon into bending or flexing actuation of an articulating finger (or other type of joint of a prosthesis). A compliant joint may alternatively be formed for actuation with non-planar actuation such as a linear actuation along some guided path or multi-angle rotation such as in a compliant ball joint. The compliant joint may be implemented for bending/joint actuation of various artificial bodies (e.g., prosthetic fingers, hands, arms, knees, legs, neck). A compliant joint can also be used for non-anthropomorphic prosthesis joints.

In some variations, a compliant joint may include multiple points of compliance or a defined region of compliance. For example, a sequence of multiple sub-regions of compliance may be integrated along a region of the monolithic bone structure. The sub-regions of compliance in combination can satisfy the motion range and resulting compliance desired to achieve the kinematic motion. In other variations, multiple compliant joints may be used in combination within one prosthesis.

As discussed, a compliant joint is preferably used by having at least one compliant body structure at a point/region of actuation. For example, a compliant body structure may extend across a rotational joint region. In one variation, the compliant body structure is a flexible body structure. Alternative variations may use other structures that provide compliance and/or a restorative force. For example, springs, pneumatic chambers, or other "flexible" mechanisms may be used. Herein, the compliant structures are described primarily as a flexible material. The flexible material may be any suitable type of flexible material and/or structure. In one implementation, flexible thermoplastic polyurethane (e.g., NinjaTek Cheetah filament) may be used.

In some variations, the compliant joint may also include rigid structures that are also integrated into the joint. The rigid structures may function as rigid bone structures. The rigid structures may be made of layers of nylon. The compliant structures may be made of flexible thermoplastic polyurethane (TPU). TPU functions to give the bone structure flexibility and impact resistance, similar to a biological ligament. The rigid structures may alternatively be made of any suitable material. As a structural support, the compliant joint constructed of nylon and TPU layers may help reduce weight of the finger while enabling torsional flexural compliance as compared to the conventional rigid joints. The nylon functions to give the compliant bone stiffness and limit bending, particularly in the distal segment of the bone. The nylon and TPU components/layers may additionally be 3D-printed when producing the compliant joint structure. Accordingly, the compliant joint structure can be partially constructed of three-dimensional printed components.

The rigid structures may provide rigidity and may be designed to guide and/or constrain actuation. For example, two rigid structures may be used on either side of a joint (emulating rigid bones) with the compliant flexible material extending across the meeting region of the rigid structures.

In one variation, the articulating prosthesis 100 includes at least one layer of a compliant structure and a rigid structure. In such variation, the articulating prosthesis 100 (or at least a joint of the articulating prosthesis 100) includes a central rigid structure flanked by a compliant flexible structure. The compliant flexible structure can be on one, two, or more sides of the rigid structure. In some variations, the compliant flexible structure may substantially surround the rigid structure. As one example, a disjointed nylon rigid structure may be oriented centrally (e.g., acting as two rigid bone structures), connected by flexible thermoplastic polyurethane layers on the lateral sides, which are continuous across the joint (acting like continuous ligaments). This exemplary implementation can follow and/or emulate the anatomy of an actual joint. Alternative approaches may alternatively be used. For example, the rigid material may be an external structure and the compliant flexible structure could be an internal structure.

In some variations, rigid structures (e.g., an internal nylon layer) meeting at a joint are disjointed, but they may alternatively mechanically couple forming a joint. In some variations, a rigid structure may not be present within select joint/bone segments of a prosthesis. For example, an artificial finger may have a compliant PIP joint where there is no internal rigid structure on the distal end of the joint. As one example, this can also apply to the hock (ankle joint) of a dog or other animal. In other alternative variations, a rigid structure may be integrated into a rigid, non-actuating joint such as a non-compliant DIP segment.

In making a multiarticulated finger, multiple compliant joints can be used in combination to create an artificial finger with multiple articulating joints. When used with a hand, the system may additionally include a base palm body and a set of articulating prosthetic fingers.

The rigid bone structure may be manufactured and assembled through a variety of techniques. As discussed, the rigid bone structure may be 3D-printed in part or whole. The rigid bone structure may alternatively be injection molded, machined, and formed through any suitable manufacturing process. Molds could similarly be 3D printed or formed using rapid manufacturing techniques. Alternatively, the molding may use standard parts where customization is provided through 3D printing of the rigid bone structure(S).

3D printing of the parts or using 3D printing for customized mold making may be leveraged to customize part creation to calibrate operation of the articulating prosthesis 100 to a user's condition. In some variations, design parameters (which may include positioning, dimensions, thicknesses of components) of the articulating prosthesis 100 may be calibrated for a user based on a mechanical model. Degree of motion and/or translation of forces may be calculated and calibrated for individual users (or particular classes for different situations). In particular, the moment arm of the joint (e.g., the perpendicular distance between the joint and artificial tendon across the meeting region of the rigid bone structures), and/or the thickness of the flexible ligament structure may be customized for different situations. Varying the thickness of the flexible ligament structure can alter the restorative forces from one or more compliant elements.

In some variations, the prosthesis may additionally include pressure sensors, which can function simulate neurological touch feedback for the users. Additionally, some variations may include a silicone casing (or other suitable material) that can encase all or a portion of the prosthesis. This may provide a more natural look and feel to the prosthesis.

The artificial tendon system 200 functions to couple, using artificial tendon-like fibers, musculoskeletal elements of a user's body with actuation input points 110 of an articulating prosthesis 100.

The artificial tendon system 200 can include an external tendon actuation interface 210 coupled to an actuation point of the articulating prosthesis 100 and musculoskeletal integrated artificial tendon(s) 230. The artificial tendon system 200 can additionally interface with an osseointegration abutment 300. The osseointegration abutment 300 and the musculoskeletal integrated artificial tendon 230 will generally be surgically implanted and installed.

In one preferred variation, the artificial tendon system 200 includes artificial tendon fibers that directly couple to and/or about at least one actuation point and one musculoskeletal integrated artificial tendon. For example, an actuation point may be mechanically coupled, through a length of fiber, to a tendon or portion of muscle at an internal AT segment forming the musculoskeletal integrated AT 230, and then mechanically couple about an actuation point 110 for an external AT segment as part of the external tendon actuation interface 210.

In some variations, the artificial tendon system 200 may include and/or support a single musculoskeletal integrated AT. However, in some variations, the artificial tendon system 200 may include and/or support a plurality of musculoskeletal integrated ATs. This plurality of ATs may both interface through a shared osseointegration abutment 300 or may have independent osseointegration abutments 300. Accordingly, the artificial tendon system may include integration with a plurality of musculoskeletal integrated ATs. A plurality of ATs may be integrated to different tendons or musculoskeletal structures of a body so as to afford different actuation control inputs to a connected articulating prosthesis 100. As one variation, a plurality of musculoskeletal integrated ATs may include a first musculoskeletal integrated artificial tendon integrated with a flexor tendon and a second musculoskeletal integrated artificial tendon integrated with an extensor tendon.

The artificial tendon functions as the element used to translate motion of a musculoskeletal element (e.g., tendon or bone) to motion of an actuation point 110. In one variation, this is done through one length of fiber (e.g., an external AT segment) that is coupled to at least one actuation point of the articulating prosthesis 100 and at least a second length of fiber (e.g., an internal AT segment) that couples to at least one musculoskeletal element.

In one variation, fibers that are 50 μm or less in diameter with appropriate tensile properties and biocompatibility may be used. Such artificial tendon fibers can be surgically fused or attached to tendon and/or muscle, and then coupled through an osseointegration abutment 300 to an external tendon-actuated prosthesis. The AT can be made of fiber or materials that preferably have suitable biocompatibility and tensile properties. As one example, the AT fiber may be made of braided Polyethylene terephthalate (PET), Nylon monofilament, or other suitable fiber materials.

In some variations, multiple distinct segments of fiber may be attached together. For example, an internal AT segment surgically attached may be tied or attached to a distinct artificial tendon fiber coupled to the articulating prosthesis 100. In another example, multiple segments of artificial tendon fiber surgically attached tied or attached to a distinct artificial tendon fiber may be joined together and couple to or about a shared actuation point 110. In another example, an internal AT segment may be surgically connected and then connect to multiple external AT segments so that, for example, one segment may actuate multiple distinct actuation points.

Other alternative variations to fiber-based ATs may make use of other alternative artificial tendon systems. For example, an artificial tendon may make use of a fluidic system (e.g., a hydraulic or pneumatic system) and/or rigid segments for translating linear motion between two points.

The osseointegration abutment 300 can be a surgically installed element that can include mechanical coupling of the musculoskeletal integrated artificial tendon and the external tendon actuation interface. As shown in FIG. 2C, an osseointegration abutment 300 may couple to the articulating prosthesis on a proximal end of the prosthesis.

In one variation, the osseointegration abutment 300 can be a tripod, quadpod, or any suitable type of titanium (or other type of material) mini-plate. The plate may include an internally defined cavity, mechanism, and/or suitable type of interface for the interfacing with an artificial tendon within and/or outside the body. In some variations, one or more artificial tendons can pass through such an internally defined cavity, mechanism or type of interface. For a finger prosthesis, this mini-plate is anchored into the distal end of the residual finger through three axes (180 degrees equidistant from each other) with 1.5 mm mini-plates and screws. This construction may enable a more stable implant concerning lateral torque movements and prevents loosening of the prosthesis during insertion/removal of the prosthetic finger.

Figure 8A:
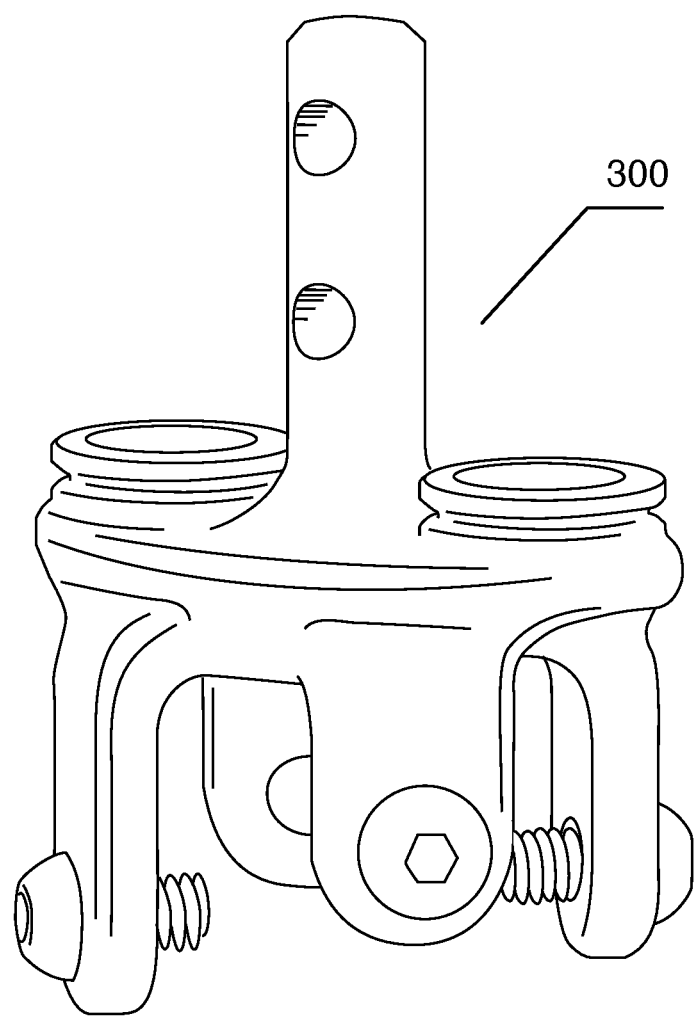
FIGS. 8A and 8B are three-dimensional schematic drawings of a variation of an osseointegration abutment.
Figure 8B:
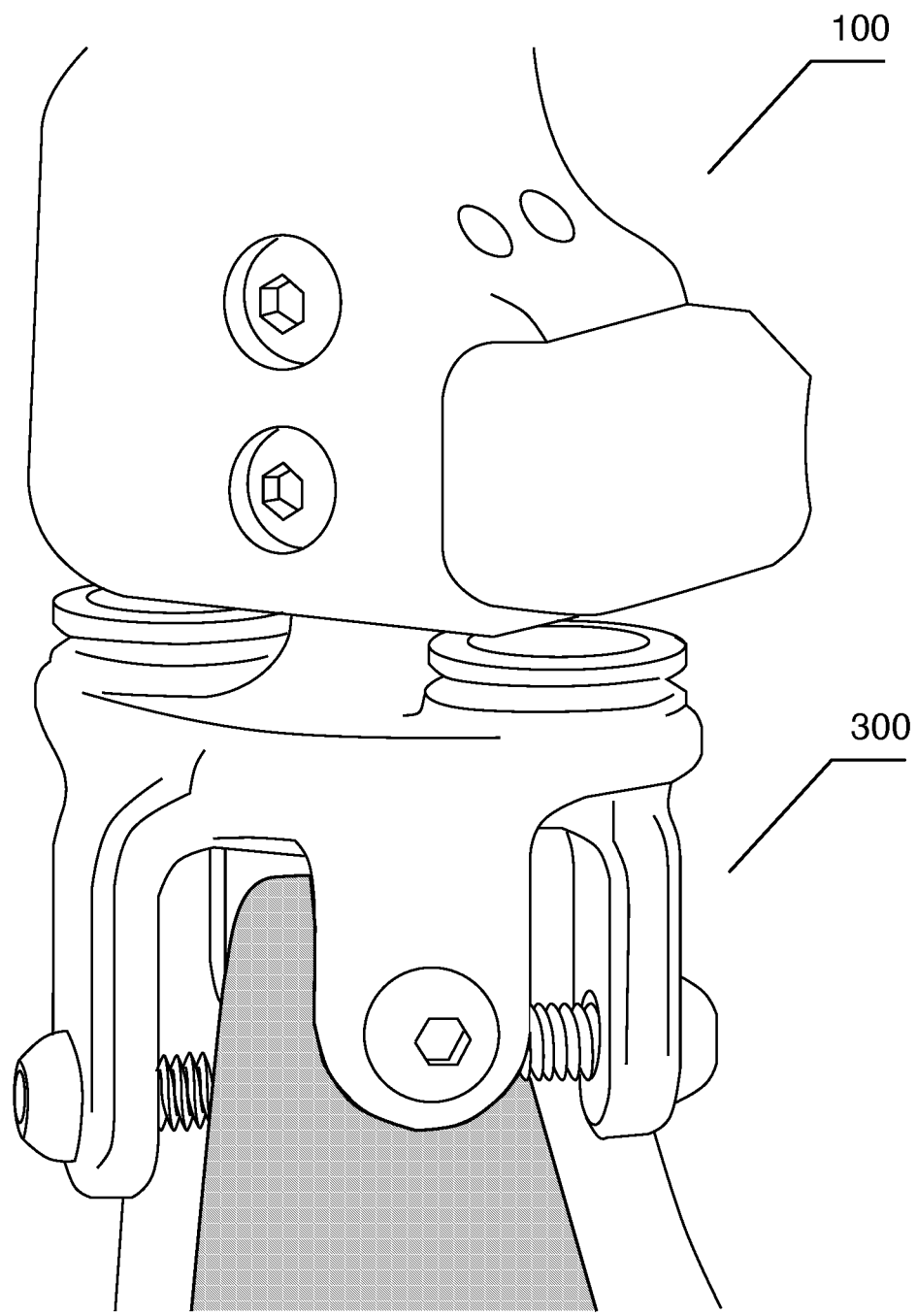

In one variation, an artificial tendon passes from within the body to outside the body through the osseointegration abutment 300. As shown in FIG. 8A, one variation of the osseointegration abutment 300 may include a set of defined through-hole cavities, through which one or more AT segment may pass. As shown in FIG. 8B, this may be used so that a set of extensor ATs can be coupled to the articulating prosthesis in one region and a set of flexor ATs can couple to the articulating prosthesis in a second region.

The system may make use of a variety of different approaches for the transition of an artificial tendon within the body to outside the body.

In one variation, the system (e.g., as part of the artificial tendon system 200) can include a channel network 220 connected to the osseointegration abutment, wherein the external tendon segment (or at least a portion thereof) being contained within the sterile channel network 220. The channel network 220 can be a tube channel. In one variation, the channel network 220 attaches proximally to the osseointegration abutment and distally to the articulating prosthesis. In other variations, the channel network 220 may route from the osseointegration abutment about the actuation point(s), and then back to the osseointegration abutment. The channel network 220 can be an integrated sterile channel network 220. Such an integrated sterile channel network 220 for the artificial tendons can use IV tubing and/or other suitable tubing. The IV tubing can attach proximally to the osseointegration abutment 300 and distally to the prosthesis (e.g., at each tendon's accurate bone insertion point). The use of IV tubing allows for the same environment within the body to exist within the prosthesis. A silicone sleeve in the shape of the prosthesis (e.g., a finger/hindlimb) may additionally be molded around the bones and artificial tendon system 200 to further protect the IV tubing and waterproof the prosthesis. In such a variation, the artificial tendons will be able to exist outside the human body and without risk of infection.

Figure 10:
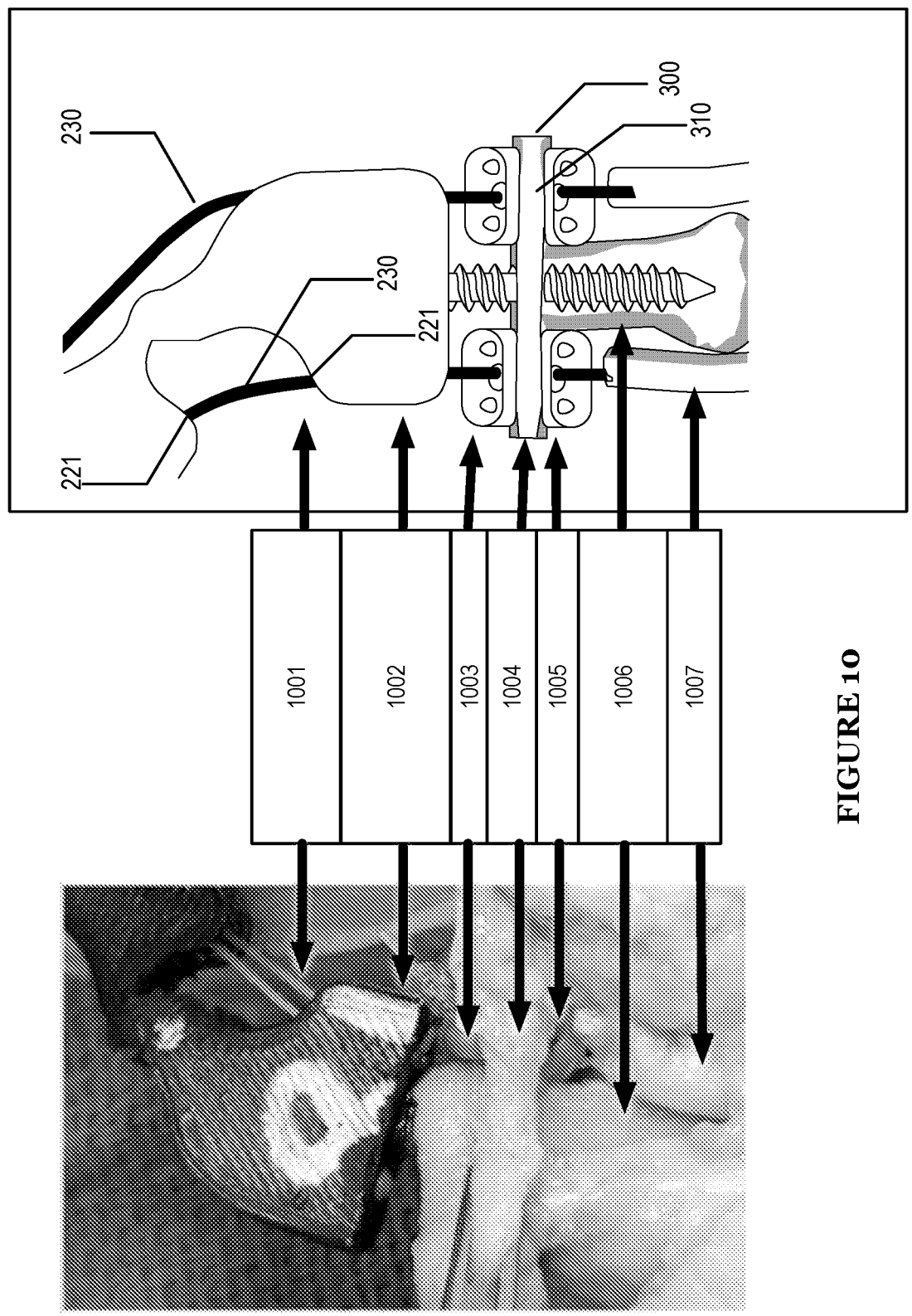
FIG. 10 shows one variation of a tendon interface that incorporates two skin flap disks with indication of an External Artificial Tendon 1001, Prosthetic Proximal Phalanx 1002, External Skin Flap Disc 1003, Skin Flap 1004, Internal Skin Flap Disc 1005, Residual Proximal Phalanx 1006, and Residual Tendon 1007.

In another variation, an additional or alternative approach of an infection mitigation system may include a mechanically fastened (e.g., crimped) artificial tendon system 200 that divides the artificial tendons into external and internal tendons. A first internal tendon segment and a first external tendon segment could be mechanically fastened together near the osseointegration abutment. In some cases as shown in FIGS. 6 and 10, the translation region 310 (e.g., the zone where the artificial tendon passthrough the osseointegration abutment) could be encased in a flexible material or use an alternative infection mitigation mechanism. For example, the external and internal tendons can be crimped together at a "crimping zone" near the osseointegration abutment 300. This may make use of a crimping technique such as a multifilament stainless steel (MFSS) single cross-lock cable-crimp system or any suitable crimping system.

The crimping zone may be sized according to the tendon excursion during actuation. For a prosthetic hand this may, for example, be around 3-5 cm in lengths. For example, one exemplary prosthesis may have a crimping zone of 4 cm for 4 cm of tendon excursion during actuation. In the example of a human finger or canine hindlimb, the crimping zone may be around 4 cm in length to account for the 4 cm of tendon excursion when the human finger or canine hindlimb is actuated. In some variations, a type of telescoping system may be used to expand to 4 cm when the tendon translates and collapse when at rest. The crimping zone may contain the only section of artificial tendon to enter/exit the body. In one variation, this section could be encased in a flexible material such as latex or other material sleeves, which may mitigate infection.

As an optional variation, the external tendons may be made out of antimicrobial material such as copper or silver. This may be used in combination with other variations such as the crimped artificial tendon system described above. This may be used in place of an encased crimping zone. Copper ions, for example, can directly damage bacterial proteins and can also induce the formation of highly damaging hydroxyl radicals which can then damage the cells via their interactions with DNA, enzymes, and other proteins, as well as the peroxidation of lipids and subsequent membrane damage.

Such a crimped tendon variation may additionally or alternatively include a fastening system that includes two skin flap discs (i.e., "fasteners") that fit together with an intermediary piece of skin situated between the two skin flap discs. The two skin flap discs may include a distal disc and a proximal disc. The two skin flap discs can be sutured or otherwise physically coupled together and through the skin, which may function to create a seal.

A loop on each skin flap disc can allow for connection to the external artificial tendons routed through the internal channels of the prosthesis, and to the internal artificial tendons attached to the residual tendons. Once attached, the system may accomplish a normal joint range of motion by actuating the internal tendons, which in turn translates the external tendons with the skin flap disc system as shown in FIG. 6. Such a variation may enable a substantially full range of motion while sealing the amputation site to mitigate risk of infection. This may be repeated for multiple tendon attachments. Though one tendon may be coupled to multiple external artificial tendons.

As shown in FIG. 10, one exemplary implementation of a variation can include an internal connection from the artificial tendon system to a skin flap over the site of the amputation, with an external artificial tendon connecting the skin flap to the external prosthesis. Such a design can keep the skin as a barrier between the external environment and the internal tissues thereby minimizing infection. Such a system can include internal and external artificial tendon segments, fastened together through the usage of two "skin flap discs", one distal of the amputation site and one proximal, allowing a piece of skin from the amputation to be sandwiched in between; the discs are sutured to one another to create a seal. Once attached, the skin flap disc system may accomplish normal joint ROM by enabling actuation of the internal tendons to translate the external tendons.

A disc used with or as OI abutment may have two connection points, an internal connection to the artificial tendon and an external connection to the prosthesis.

In some variations, the OI abutment may include a sealed flexible film pocket. Fastened around the disc may be a non-porous material used as part of the sealed film pocket that extends distally to the external port of the OI abutment. The material may be secured, which functions to create a seal around both the disc and OI abutment, thus creating a pocket within the finger as shown in FIG. 6. The length of this pocket may be approximately 1.5-2 cm in length to accommodate the necessary tendon excursion for normal finger ROM. One knowledgeable in the art would appreciate that such values may vary and could depend on different tendon actuation lengths. In some variations, the pocket (e.g., a sealed flexible film pocket) could additionally extend through the metacarpals and into the forearm region. The skin at the amputation site can be sutured around the external circumference of the OI abutment and left to heal. This system variation can create two ports into the human body without risk of infection due to a non-porous, impermeable layer of material. This approach may accomplish normal joint range of motion by transferring internal tendon actuation to external tendon translation.

In another variation, the system may include an encasement that encases the entire prosthesis (or at least portions) in a durable, yet flexible material that will resist any contamination, therefore limiting the risk for infection.

In another variation, a sealed interface may allow the internal portions of the artificial tendon to couple to the external portions of an artificial tendon at a sealed interface at the osseointegration abutment 300. For example, a sealed biocompatible and flexible and/or telescoping mechanism can cover the region (310) where the internal and external tendons couple, thereby isolating the external artificial tendon from the internal body. The flexible seal mechanism can allow the tendons to move with some degree of motion such that motion and forces can be directly translated, but the flexible seal mechanism can mitigate exposing the body to the external environment.

In another variation, an alternative mechanism may be used that mechanically translates (indirectly) artificial tendon motion within the body to linear motion applied to an external artificial tendon. For example, a gear mechanism or fluidic system may be used so that this translation of motion can be made within the housing of the osseointegration abutment 300.

In variations that include biointegration of an AT, at least one artificial tendon will pass through and/or be attached through the osseointegration abutment 300. In some variations, multiple artificial tendons will pass through or be attached through the osseointegration abutment 300.

As another aspect, the osseointegration abutment 300 may include a rigid mounting element to which the articulating prosthesis 100 can rigidly attach to the body. This can include a threaded mount or other type of static mechanical fixture. The articulating prosthesis 100 can attach to the mechanical fixture. Alternatively, other mounting solutions may be used such as a socket or sleeve.

Figure 7:
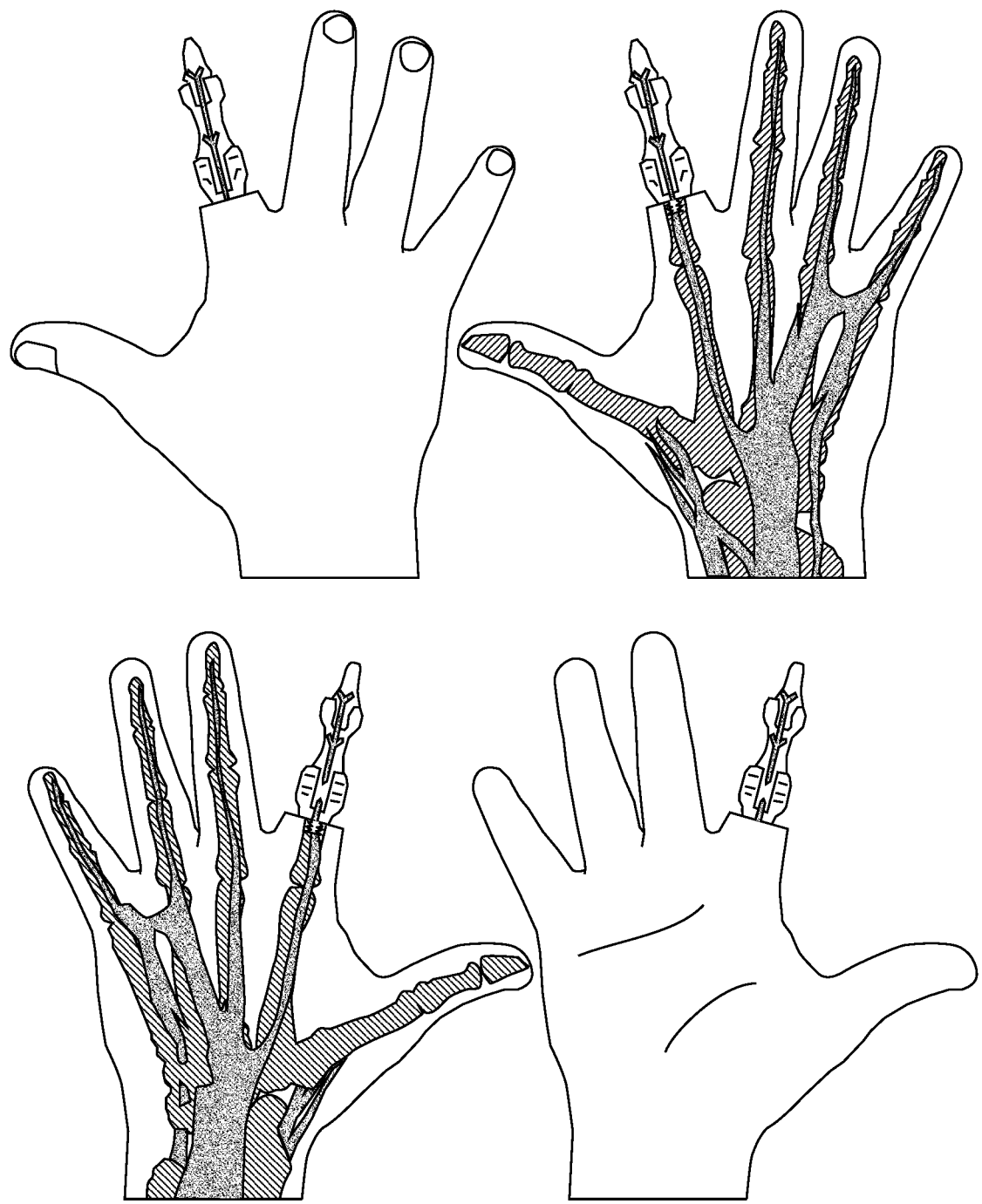
FIG. 7 is a diagram illustrating installation of a system variation.

As mentioned, the system may be particularly useful in enabling tendon/muscle-driven articulating finger prostheses. In one exemplary implementation, FIG. 7A shows a posterior view of finger prosthesis implantation into a realview hand; FIG. 7B shows a dorsal view accentuating extensor tendon connection into finger prosthesis and artificial tendon system; FIG. 7C shows an anterior view accentuating flexor tendon connection into finger prosthesis and artificial tendon system; and FIG. 7D shows an anterior view of finger prosthesis implantation into a realview hand.

In some variations, the system may be applied to emulate directly (or at least in part) the anatomy of the hand. The system may be adapted to make use of artificial tendons, and joint mechanisms of an artificial prosthesis that correspond to various joints, bones, and tendons of the human finger.

The human finger consists of three major bones and three major joints. The proximal phalanx (PP), middle phalanx (MP) and distal phalanx (DP) are the finger bones, while the metacarpophalangeal (MCP), proximal interphalangeal (PIP), and distal interphalangeal (DIP) are the finger joints. Alongside the bones and joints are two major sets of tendons: the flexors and extensors. The flexor tendons are found on the palmar side of the fingers while the extensors are on the dorsal side. The flexor digitorum superficialis (FDS) and flexor digitorum profundus (FDP) are responsible for finger flexion while the long extensor tendon is responsible for finger extension. The FDS splits into two heads across the PP and inserts into the base of the MP. This splitting of the FDS allows the FDP to pass through and insert into the base of the DP. The long extensor tendon follows a similar pattern of splitting; however, it splits itself into three bands across the PP: two lateral and one central band. The central band inserts at the base of the MP while the two lateral bands go on to insert at the base of the DP. These insertion points may ultimately determine each tendon's relative contribution to finger motion.

Finger motion is accomplished by both the muscles and tendons. The tendons may attach proximally to the forearm muscles and distally to their corresponding finger bones. Muscle contraction actuates the tendons, causing them to translate, resulting in finger motion. Once the tendons begin to translate, there are anatomical structures within the finger to ensure they do so in an efficient manner. Tendon flexor pulleys exist to prevent bowstringing and provide a smooth, frictionless surface for the tendons to glide. Fingers consist of five pulleys: one along the length of each phalanx and one at each joint. The analog for flexor pulleys is extensor hoods which wrap around the phalanges from the dorsal side to hold the extensor tendons in place during their translation. In some variations, the system may incorporate the finger pulleys and extensor hoods within the design of our prosthesis. This may be achieved by mirroring functionality of mechanics by guiding tendon movement, and not necessarily mirroring structure.

3. Method

A method for enabling an artificial tendon/muscle-driven prosthesis can, in some variations, include coupling an articulating prosthesis to surgically attached artificial tendons. The method is preferably used in the attachment and setting up operation of a system such as the one described above.

Figure 11:
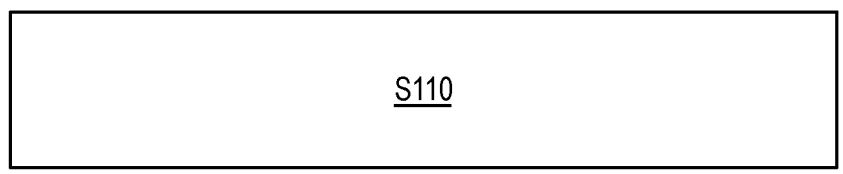
FIG. 11 is a flowchart of a method for configuring a tendon-driven prosthesis.
Figure 11:
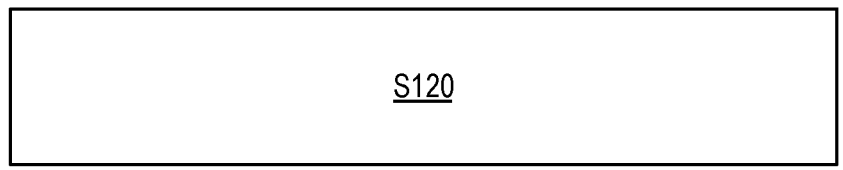
Figure 11:
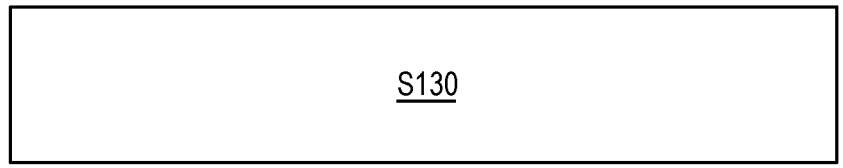

Coupling an articulating prosthesis to surgically attached ATs can include connecting an articulating prosthesis to an artificial tendon system. This can include connecting or otherwise biointegrating an internal AT segment to a body of a user S110, interfacing the internal AT segment with an external AT segment S120, and coupling the external AT segment about an actuation point of the articulating prosthesis S130 as shown in FIG. 11.

Connecting or biointegrating the internal AT segment to the body of a user functions to couple the AT system to a controllable element of a user's body. The method may include surgically integrating the musculoskeletal integrated artificial tendon, and surgically installing the osseointegration abutment. In some variations, surgical biointegration of a system for a tendon/muscle-driven prosthesis may involve a 2-stage surgery, for example. The surgical procedure(s), in some variations, may include attaching the AT system, implanting the OI abutment, and constructing or otherwise establishing the infection mitigation system. Once the artificial tendon system has successfully tissue-integrated with the existing tendon or muscle, the abutment has sufficiently osseointegrated, and the infection mitigation system has been properly integrated with the OI abutment, the prosthesis (e.g., a prosthetic finger) can then be attached.

Coupling the external AT segment about an actuation point of the articulating prosthesis functions to connect an external AT segment with a prosthesis. This may include channeling an external AT fiber segment through one or a set of channels of the prosthesis. In one variation, the AT fiber segment may be rigidly attached to the prosthesis. In another variation, the AT fiber segment may route or loop through a series of channels such that a formed loop of the AT segment can produce actuation. In some variations, the channels may be sterilized as part of an infection mitigation mechanism of the system.

Interfacing the internal AT segment with an external AT segment S120 functions to mechanically link motion at one AT segment to the other AT segments.

In one variation, one internal AT segment is directly interfaced with an external AT segment. This can enable movement of the tendon, muscle, or bone to directly control actuation of one external AT segment.

In another variation, one internal AT segment may interface with a set of external AT segments. This can enable movement of one tendon, muscle, or bone to impact actuation of multiple joints. For example, an AT may route about a DIP and PIP actuation points of a finger such that one biointegrated AT can be used to control actuation of both joints. As an alternative variation, an AT may be used to actuate distinct actuation points.

In another variation, multiple AT segments may be biointegrated at different sites, and interface with a shared external AT segment.

Similarly, any number of distinct ATs may be used in combination with a prosthesis. For example, 2-3 sets of tendon systems may be used and interface through a shared abutment or distinct abutments.

Figure 12:
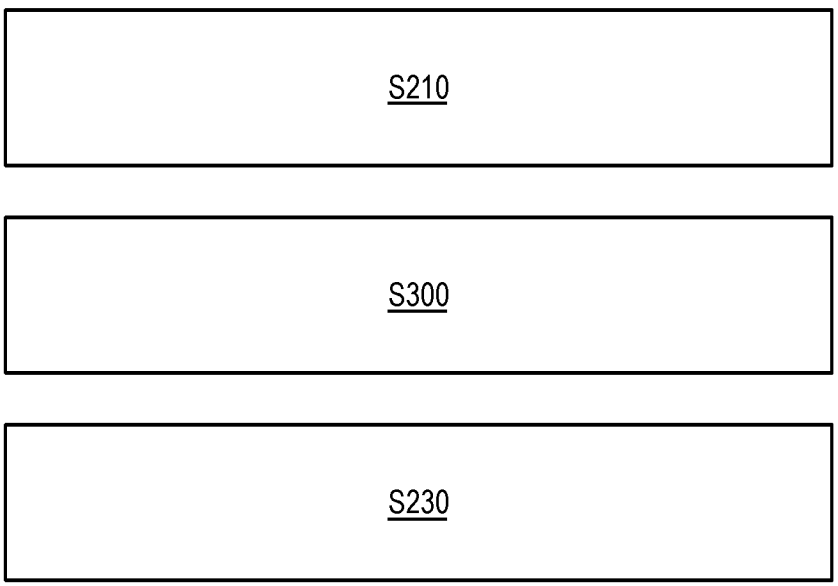
FIG. 12 is a flowchart of a method for calibrating a tendon-driven prosthesis.

In one variation, a method variation may include customizing the mechanical design of the articulating prosthesis, which may be used in combination with the method for integrating a tendon/muscle-driven prosthesis with a user. Such a customization variation of the method may include, as shown in FIG. 12, measuring musculoskeletal conditions of a user S210, modeling mechanical coupling of the articulating prosthesis to one or more musculoskeletal elements of the user and determining at least one mechanical design parameter of the articulating prosthesis S220, and manufacturing at least one mechanical element using the mechanical design parameter S230.

When customizing the system for a patient, one or more parameters of the system may be customized and adjusted to the particular patient. Examples of possible aspects that could be customized could include: the number of fibers in the artificial tendons, the size of the osseointegration abutment, the individual dimensions of the prosthesis, tab length on an OI abutment, screw orientation, if a hybrid design is used then the length of the intramedullary component, the length of each prosthetic bone/body segment, the compliance/thickness of materials at each joint, the amount of silicone around the bone after encasement, the size of ports, the method for attaching a flexible film to the discs and OI abutment, the type of material for the external tendons, the channel placement to accommodate different joint torques, the tendon-to-bone insertion points, and/or other parameters.

The process of modeling mechanical coupling of the articulating prosthesis to one or more musculoskeletal elements of the user may include calculating design parameters of at least one element of the prosthesis for at least one performance condition.

The performance condition can include actuation range of motion. In other words, the modeling may determine one or more design parameters that can be customized so that translation of a musculoskeletal element translates to some amount of motion of a joint. The amount of motion may be a range determined to be suitable or potentially that can be controlled by a trained technician. In particular the moment arm of the joint (e.g., the diameter of pulley where a tendon interfaces with an actuation point) can be calculated so that the range of motion of an artificial finger can be calibrated.

An alternative or additional performance condition can include force translation. Modeling for force translation functions to attempt to make it so that the input force by a user is tuned to the amount of force applied by the prosthesis. The tuning can be for approximate force where they are made substantially equivalent (e.g., force input to force output is within 10%). Tuning may, in some variations, be used so that the force can be customized to be more proportional. As one example, the thickness of the rigid bone structure may be customized to alter the restorative force in a compliant joint. Alternatively, the amount, size, design, material, and/or other aspects of a compliant or restorative element may similarly be altered to tune the forces.

In one variation, a 3D scan, X-ray, schematic, or set of measurement parameters can be entered into a specialized computer system such that an appropriate articulating prosthesis can be generated.

3D printing of the parts or using 3D printing for customized mold making may be leveraged to customize part creation to calibrate operation of the articulating prosthesis to a user's condition. Degree of motion and/or translation of forces may be calculated and calibrated for individual users (or particular classes for different situations).

As used herein, first, second, third, etc. are used to characterize and distinguish various elements, components, regions, layers and/or sections. These elements, components, regions, layers and/or sections should not be limited by these terms. Use of numerical terms may be used to distinguish one element, component, region, layer and/or section from another element, component, region, layer and/or section. Use of such numerical terms does not imply a sequence or order unless clearly indicated by the context. Such numerical references may be used interchangeable without departing from the teaching of the embodiments and variations herein.

As a person skilled in the art will recognize from the previous detailed description and from the figures and claims, modifications and changes can be made to the embodiments of the invention without departing from the scope of this invention as defined in the following claims.

We claim:

1. A system comprising:
   an articulating prosthesis comprising a set of actuation points and a set of defined tendon routing channels defined through a body structure of the articulating prosthesis;
   an osseointegration abutment comprising a sealed flexible film pocket made of an impermeable material;
   an artificial tendon system, the artificial tendon system being integrated with the articulating prosthesis and comprising:
   an external tendon actuation interface coupled relative to at least one actuation point of the set of actuation points and that comprises at least one external artificial tendon segment routed through one of the set of defined tendon routing channels, and
   an internal artificial tendon segment, wherein the external artificial tendon segment is coupled to the internal artificial tendon segment through the sealed flexible film pocket of the osseointegration abutment.

2. The system of claim 1, wherein the osseointegration abutment is an interface with tendon passthrough actuation.

3. The system of claim 2, wherein the artificial tendon system comprises a plurality of artificial tendons, each artificial tendon comprising that each include at least one respective internal artificial tendon segment and at least one respective external artificial tendon segment.

4. The system of claim 1, further comprising a channel network that connects to the osseointegration abutment and wherein the external artificial tendon segment is contained within the channel network.

5. The system of claim 1, wherein the osseointegration abutment comprises an internally defined interface through which an artificial tendon of the artificial tendon system passes.

6. The system of claim 1, further comprising, relative to the at least one actuation point, a proximal channel and a distal channel defined in the articulating prosthesis and through which the external artificial tendon segment of the external tendon actuation interface passes.

7. The system of claim 1, further comprising a pair of channels defined in the articulating prosthesis and through which the external artificial tendon segment of the external tendon actuation interface is routed through one side of the pair of channels, routed about an actuation point, and routed back through the opposing side of the pair of channels, wherein opposing ends of the external artificial tendon segment are terminated at substantially the same site.

8. The system of claim 1, wherein the set of actuation points is a single actuation point integrated with the artificial tendon system.

9. The system of claim 1, wherein the set of actuation points comprises a plurality of actuation points that are integrated with the artificial tendon system.

10. The system of claim 9, wherein the articulating prosthesis comprises a prosthetic finger, and wherein the external tendon actuation interface further comprises a second external artificial tendon segment, and wherein the external artificial tendon segment is coupled relative to a distal interphalangeal actuation point of the prosthetic finger and the second external artificial tendon segment is coupled relative to a proximal interphalangeal actuation point of prosthetic finger.

11. The system of claim 9, wherein the articulating prosthesis comprises a prosthetic finger, and wherein the external artificial tendon segment coupling relative to a distal interphalangeal actuation point of the prosthetic finger and a proximal interphalangeal actuation point of prosthetic finger.

12. The system of claim 9, wherein the external tendon actuation interface further comprises a second external artificial tendon segment, and wherein the external artificial tendon segment coupling is coupled relative to a first actuation point of a first actuating digit of the articulating prosthesis and the second artificial tendon segment is coupled relative to a second actuation point of a second actuating digit of the articulating prosthesis.

13. The system of claim 1, wherein the internal artificial tendon segment is configured to integrate with a musculoskeletal structure.

14. The system of claim 13, wherein the artificial tendon system further comprises a second internal artificial tendon segment, wherein the first internal artificial tendon segment is configured to interface with a flexor tendon and the second internal artificial tendon segment is configured to interface with an extensor tendon.

15. The system of claim 1, wherein the first actuation point is a compliant joint comprising a living hinge.

16. The system of claim 15, wherein the osseointegration abutment comprises an internally defined interface through which an artificial tendon of the artificial tendon system passes.

17. A system for a prosthetic finger comprising:
   a prosthetic finger with a body structure including a first actuation point, a set of tendon routing channels defined through the body structure, the set of routing channels comprising pairs of channels in a proximal segment before the first actuation point and in a distal segment after the first actuation point, wherein the first actuation point is a compliant joint in the prosthetic finger with a flexible material formed as a living hinge at the actuation point;
   an osseointegration abutment comprising a sealed flexible film pocket made of an impermeable material; and
   an artificial tendon system that comprises:
   a first external tendon segment that is routed through a first side of the pairs of channels and loops back at or after the first actuation point and is routed through a second side of the pairs of channels, and
   an internal artificial tendon segment, wherein the first external artificial tendon segment is coupled to the internal artificial tendon segment through the sealed flexible film pocket of the osseointegration abutment.

* * * * *